(12) United States Patent
Stallcup et al.

(10) Patent No.: US 7,214,510 B2
(45) Date of Patent: May 8, 2007

(54) REGULATION OF GENE EXPRESSION BY PROTEIN METHYLATION

(75) Inventors: Michael R. Stallcup, Los Angeles, CA (US); Dagang Chen, Hacienda Heights, CA (US); Heng Hong, Carlmel, IN (US); Dana W. Aswad, Irvine, CA (US)

(73) Assignees: Regents of the University of California, Oakland, CA (US); The University of Southern California, Los Angeles, CA (US)

( * ) Notice: Subject to any disclaimer, the term of this patent is extended or adjusted under 35 U.S.C. 154(b) by 251 days.

(21) Appl. No.: 10/830,591

(22) Filed: Apr. 22, 2004

(65) Prior Publication Data

US 2005/0176092 A1    Aug. 11, 2005

Related U.S. Application Data

(62) Division of application No. 09/464,377, filed on Dec. 15, 1999, now Pat. No. 6,743,614.

(60) Provisional application No. 60/112,523, filed on Dec. 15, 1998.

(51) Int. Cl.
*C12P 21/00* (2006.01)
*C07K 1/113* (2006.01)
*C12N 9/10* (2006.01)

(52) U.S. Cl. .......... 435/68; 435/193; 530/402
(58) Field of Classification Search ........... 435/68, 435/193; 530/402
See application file for complete search history.

(56) References Cited

U.S. PATENT DOCUMENTS 6,060,250 A    5/2000  Lal et al.

OTHER PUBLICATIONS

GenBank Accession No. AA 396116, Apr. 25, 1997.
GenBank Accession No. AA215095, Feb. 3, 1997.
Chen et al. "Regulations of Transcription by a Protein Methyltransferase" *Science* (1999) 284:2174-2177.
Han et al. "Multiple Signal Input and Output Domains of the 160-Kilodalton Nuclear Receptor Caoctivator Proteins" *Molecular and Cellular Biology* (1999) 19:6164-6173.

*Primary Examiner*—Rebecca Prouty
(74) *Attorney, Agent, or Firm*—Foley & Lardner LLP

(57) ABSTRACT

The invention relates to the cDNA and deduced amino acid sequence of the Coactivator Associated arginine (R) Methyltransferase protein, CARM1. A method is described for the use CARM1 to regulate gene expression in vivo. CARM1 has also been used to methylate arginine residues of histones, synthetic peptides, and other proteins. A method to use CARM1 to screen for drugs that inhibit its methyltransferase activity is also described, as is a method to screen for drugs that modulate CARM1's interactions with other proteins.

2 Claims, 11 Drawing Sheets

Figure 1

```
SEQ ID NO:1    CARM1   168  VRTGTYQRAILQNHTDFKDKIVLDVGCGSGILSFFAAQAG.ARKIYAVEASTMAQHAEVL 226
SEQ ID NO:3    CARM1   168  VRTGTYQRAILQNHTDFKDKIAAAVGCGSGILSFFAAQAG.ARKIYAVEASTMAQHAEVL 226
SEQ ID NO:7    hPRMT1   52  ---L--RNSMFH-RHL----V-----S-T---CM---K--.---VIGI-C-SISDY-VKI 111
SEQ ID NO:8    hPRMT2  120  P--TK-HSV----KESLT--VI------T----L-C-HYARP-AV------E----TGQ- 179
SEQ ID NO:9    hPRMT3  219  I--ES-RDF-Y--PHI----V-------T----M---K--.-K-VLG-DQ-EILYQ-MDI 277
SEQ ID NO:10   yODP1    41  ---LS-RN-----KDL------------T----M---KH-.-KHVIG-DM-SIIEM-KE- 99

SEQ ID NO:1    CARM1   227  VKSNNLTDRIVVIPGKVEEVSLP.EQVDIIISEPMGYMLFNERMLESYLHAK.KYLKPSG 284
SEQ ID NO:3    CARM1   227  VKSNNLTDRIVVIPGKVEEVSLP.EQVDIIISEPMGYMLFNERMLESYLHAK.KYLKPSG 284
SEQ ID NO:7    hPRMT1  112  --A-K-DHVVTI-K------E--V-K--------W---C-Y-S---NTV---RD-W-A-D- 171
SEQ ID NO:8    hPRMT2  180  -LQ-GFA-I-T-YQQ---D-V--.-K--VLV--W--TC-LF-F-I--I-Y-RDAW--ED- 238
SEQ ID NO:9    hPRMT3  278  IRL-K-E-T-TL-K-I----H--V-K--V----F-LF-S--D-V-Y--N---AKG- 337
SEQ ID NO:10   yODP1   100  -EL-GFS-K-TLLR-L--D-H--FPK-------W---F-LY-S-MDTV-Y-RDH-.VEG- 159
```

FIGURE 3
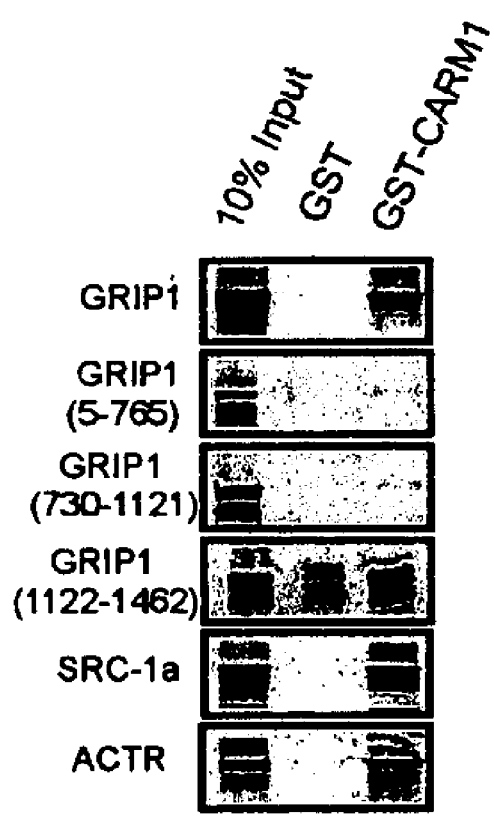
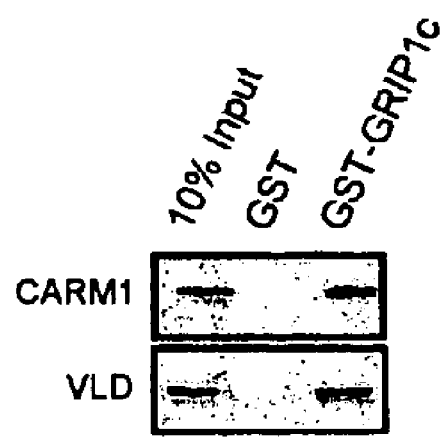

FIGURE 5
A
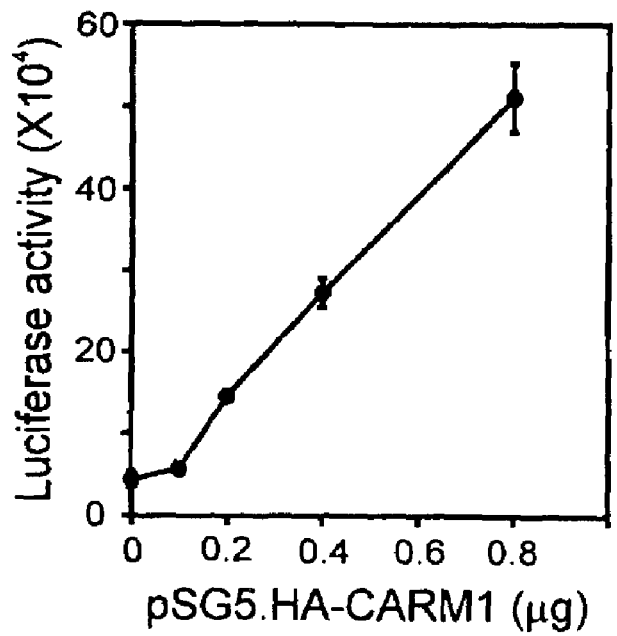
B
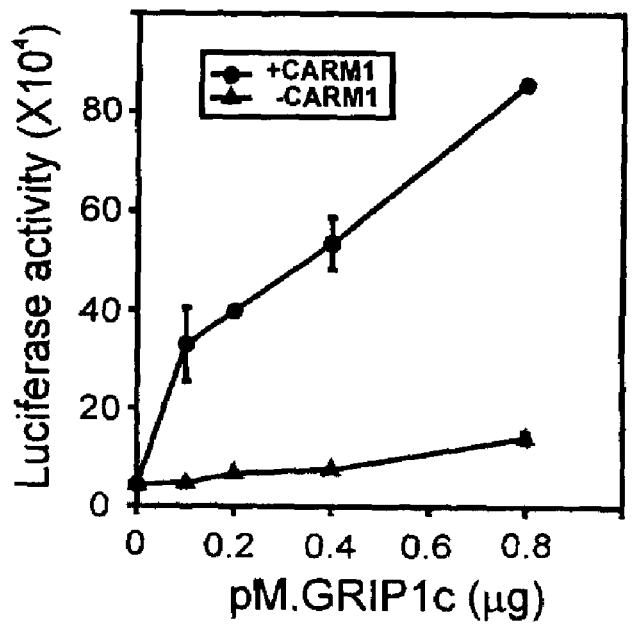

FIGURE 6
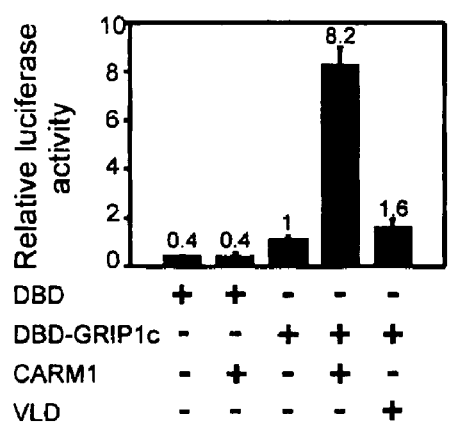
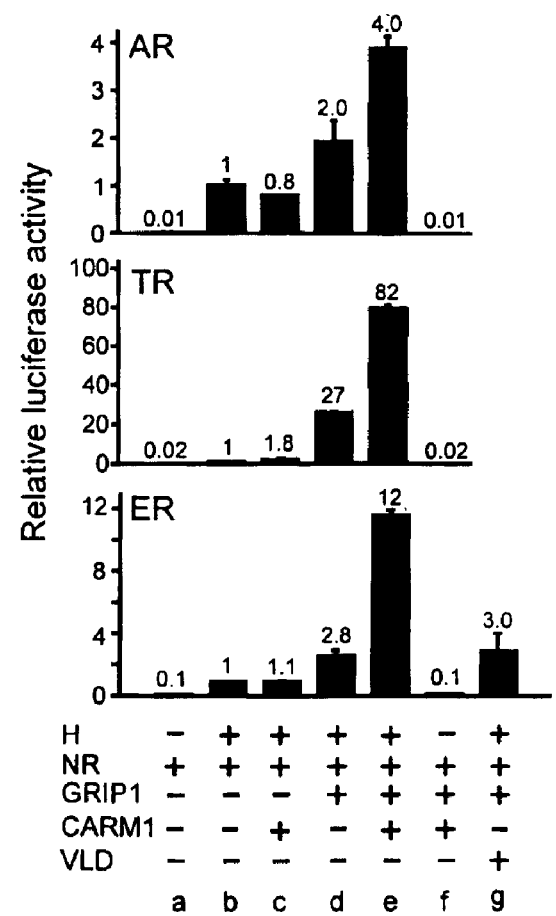

Model: a Role for Protein Methylation
in Transcriptional Regulation

FIGURE 8
Protein Methyltransferase Activity
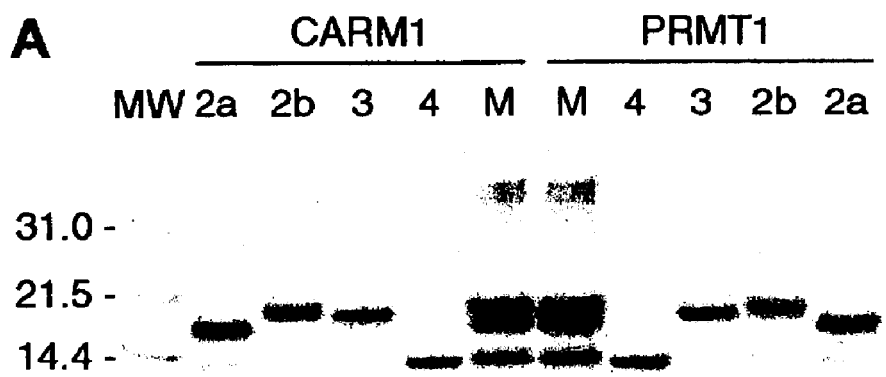
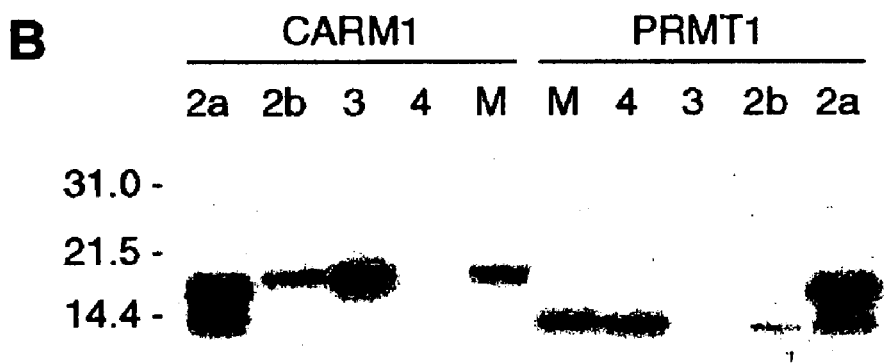
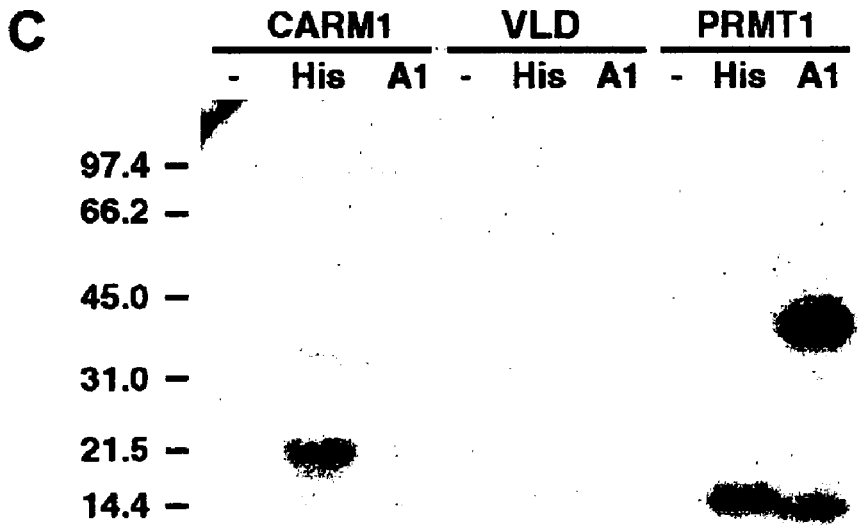

FIGURE 10
A
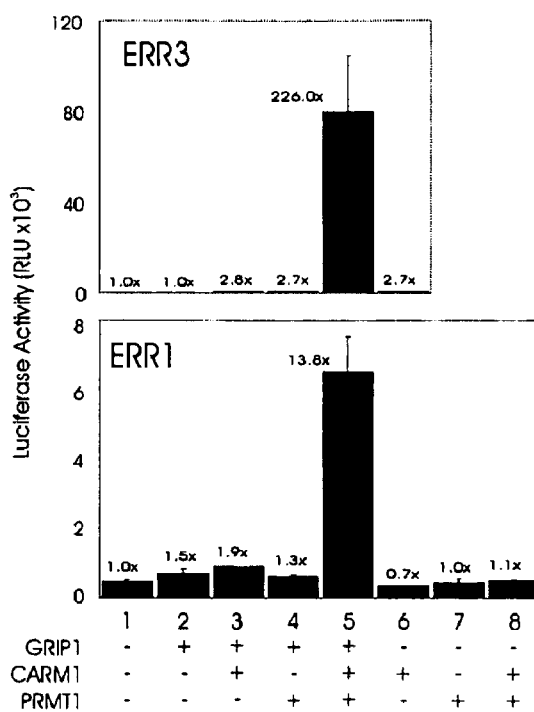
B
Synergy among three coactivators with different levels of ER
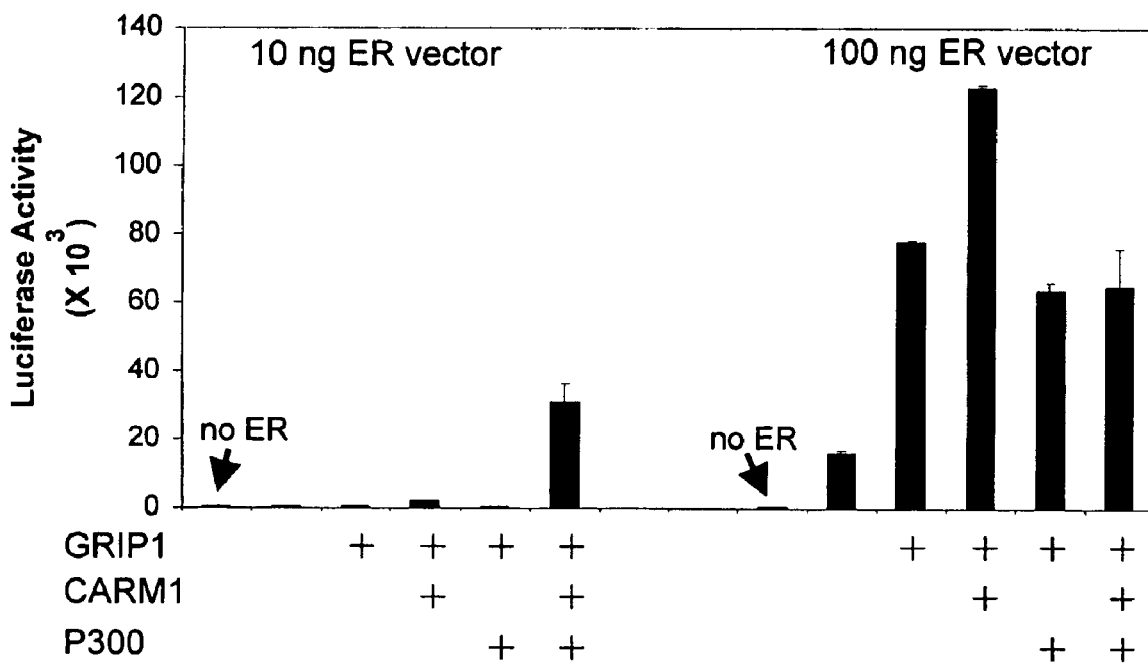

REGULATION OF GENE EXPRESSION BY PROTEIN METHYLATION

RELATED APPLICATION DATA

This application is a divisional of U.S. application Ser. No. 09/464,377, filed Dec. 15, 1999, now U.S. Pat. No. 6,743,614 issued Jun. 1, 2004, which in turn claims priority to provisional application Ser. No. 60/112,523, filed Dec. 15, 1998, the entire disclosures of which is are hereby incorporated by reference.

GOVERNMENT SUPPORT

The government may have certain rights in this invention pursuant to grants DK43093 and NS17269 from the National Institutes of Health.

FIELD OF THE INVENTION

The invention relates to coactivators of transcription and to proteins with protein methyltransferase activity.

BACKGROUND

The activities of all cells are conducted primarily by the thousands of different types of proteins each cell produces. The blueprint or code for synthesizing each protein is found in a corresponding gene, i.e., each gene encodes the information needed to synthesize a specific protein. Gene "expression" results in the production of the protein by a stepwise mechanism that includes 1) "transcription" of the gene by RNA polymerase to produce a messenger RNA (mRNA) that contains the same protein-encoding information; and 2) "translation" of the mRNA by ribosomes to produce the protein. Each gene is expressed in specific tissues and at specific times during the life of the organism. Expression of most genes is regulated in response to a variety of signals that arise either outside or inside the organism. This pattern of specific expression for each gene is determined by the "promoter region" of each gene, which is located adjacent to the protein-encoding region of the gene. Each gene's promoter contains many "regulatory elements." Each regulatory element serves as a binding site for a specific protein, and the binding of the appropriate protein to a specific regulatory element can cause enhancement or repression of gene expression. Together, the regulatory elements and the proteins that bind to these elements determine the expression pattern for the specific gene.

Hormones represent one of the most important mechanisms for communication between different organs and tissues in multicellular organisms. In mammals, hormones are synthesized in one organ or tissue, and travel through the blood stream to various target organs. By interacting with specific receptor proteins in the target cells, the hormones change the activities of the cell. Frequently the cellular effects of the hormone include changes in the expression of specific genes. The protein products of these genes then carry out the biological actions that result in altered cellular functions.

The effects of one extremely important class of hormones are carried out by a family of related receptor proteins called the nuclear receptors (Evans, R. M. (1988) *Science* 240: 889–895; Tsai, M-J. and B. W. O'Malley (1994) *Annu. Rev. Biochem.* 63:451–486; Beato, M., et al. (1995) *Cell* 83:851–857). This family of proteins includes the receptors for all of the steroid hormones, thyroid hormones, vitamin D, and vitamin A, among others. The family also includes a large number of proteins called "orphan receptors" because they do not bind any hormone or because the hormone that binds to them is unknown, but they are nevertheless structurally and functionally related to the hormone-binding nuclear receptors. Nuclear receptors are transcriptional regulatory proteins that act by a common mechanism. For those nuclear receptors that do bind hormones, the appropriate hormone must enter the cell and bind to the nuclear receptors, which are located inside the target cells. The activated nuclear receptors bind to specific regulatory elements associated with specific genes that are regulated by these proteins. Binding of the activated nuclear receptors to the regulatory elements helps to recruit RNA polymerase to the promoter of the gene and thereby activates expression of the gene. This mechanism also applies to many of the orphan nuclear receptors.

After nuclear receptors bind to a specific regulatory element in the promoter of the gene, they recruit RNA polymerase to the promoter by a mechanism which involves another group of proteins called coactivators, that are recruited to the promoter by the nuclear receptors (Horwitz, K. B. et al. (1996) *Mol. Endrocrinol.* 10:1167–1177; Glass, C. K. et al. (1997) *Curr. Opin. Cell Biol.* 9:222–232). The complex of coactivators helps the receptors to activate gene expression by two different mechanisms: 1) they make the gene more accessible to RNA polymerase by unfolding the "chromatin." Chromatin is composed of the DNA (which contains all the genes) and a large group of DNA-packaging proteins. To unfold chromatin some of the coactivator proteins contain an enzymatic activity known as a histone acetyltransferase (HAT). HAT proteins transfer an acetyl group from acetyl CoA to the major chromatin proteins, which are called "histones." Acetylation of the histones helps to unfold chromatin, thus making the gene and its promoter more accessible to RNA polymerase. 2) The coactivators and the nuclear receptors make direct contact with a complex of proteins called basal transcription factors that are associated with RNA polymerase; this interaction recruits RNA polymerase to the promoter. Once RNA polymerase binds to the promoter, it initiates transcription, i.e., synthesis of mRNA molecules. The final activation of RNA polymerase after it binds to the promoter may also require some intervention by the coactivator proteins, but little is known about the mechanism of these final steps of transcriptional activation.

One specific family of three related coactivator proteins, the "nuclear receptor coactivators" or "p160 coactivators" (because their mass is approximately 160 kilodaltons), are required for the gene activation activities of many of the nuclear receptor proteins. The three related nuclear receptor coactivators are GRIP1, SRC-1, and p/CIP; all three proteins also have additional names that are used by some investigators (Onate, S. A. et al. (1995) *Science* 270:1354–1357; Hong, H. et al. (1996) *Proc. Natl. Acad. Sci. USA* 93:4948–4952; Voegel, J. J. et al. (1996) *EMBO J.* 15:3667–3675; Kamei, Y. et al. (1996) *Cell* 85:403–414; Torchia, J. et al. (1997) *Nature* 387:677–684; Hong, H. et al. (1997) *Mol. Cell. Biol.* 17:2735–2744; Chen, H. et al. (1997) *Cell* 90:569–580; Anzick, S. L. et al. (1997) *Science* 277: 965–968; Li, H. et al. (1997) *Proc. Natl. Acad. Sci. USA* 94:8479–8484; Takeshita, A. et al. (1997) *J. Biol. Chem.* 272:27629–27634). These coactivators are recruited directly by the DNA-bound nuclear receptors. The nuclear receptor coactivators, in turn, recruit other coactivators, including CBP (or p300) and p/CAF (Chen, H. et al. 1997). All of these coactivators have been shown to play roles in gene activation by one or both of the two mechanisms mentioned above. Some of them have HAT activities to help unfold chromatin structure (Chen, H. et al. 1997; Spencer, T. E. et al. (1997). *Nature* 389:194–198), and others have been shown to make direct contact with proteins in the RNA polymerase complex (Chen, H. et al. 1997; Swope, D. L. et al. (1996) *J. Biol. Chem.* 271:28138–28145). Thus, the discovery and characterization of these coactivators provides a better understanding of the mechanism by which nuclear receptors activate gene transcription.

Histones are known to be methylated as well as acetylated (Annunziato, A. T. et al. (1995) *Biochem.* 34:2916; Gary J. D. and Clarke, S. (1998) *Prog. Nucleic Acids Res. Mol. Biol.* 61:65). However, the function of histone methylation is unknown. Methylation of histone H3, is a dynamic process during the lifetime of histone molecules, and newly methylated H3 is preferentially associated with chromatin containing acetylated H4 (Annunziato, A. T. et al. 1995); thus methylation of H3, like acetylation of H4, is associated with active chromatin. In other studies lysine methylation of histones has been found in a variety of organisms; arginine methylation of histones, while not clearly documented in mammals, has been demonstrated in other classes of organisms (Gary and Clarke 1998). In *Drosophila* cells heat shock treatment causes increased arginine methylation of histone H3, which could be associated with activation of heat shock genes or repression of the other genes (Desrosiers, R. and R. M. Tanguay (1988) *J. Biol. Chem.* 263:4686).

Proteins can be N-methylated on amino groups of lysines and guanidino groups of arginines or carboxymethylated on aspartate, glutamate, or the protein C-terminus. Recent studies have provided indirect evidence suggesting roles for methylation in a variety of cellular processes such as RNA processing, receptor mediated signaling, and cellular differentiation (Aletta, J. M. et al. (1998) *Trends Biochem. Sci.*: 23:89; Gary and Clarke 1998). However, for the most part the specific methyltransferases, protein substrates, and specific roles played by methylation in these phenomena have not been identified. Two types of arginine-specific protein methyltransferase activities have been observed, type I and type II. Genes for three mammalian and one yeast type I enzymes, which produce monomethyl and asymmetric dimethylarginine residues previously have been identified (FIG. 1). On the other hand, type II protein arginine methyltransferases produce monomethyl and symmetric dimethylarginine residues. In vitro protein substrates for various protein arginine methyltransferases include histones and proteins involved in RNA metabolism such as hnRNPA1, fibrillarin, and nucleolin (Lin, W-J. et al. (1996) *J. Biol. Chem.* 271: 15034–15044; Gary, J. D. et al. (1996) *J. Biol. Chem.* 271:4585; Najbauer, J. et al. (1993) *J. Biol. Chem.* 268: 10501–10509). The arginine residues methylated in many of these proteins are found in glycine-rich sequences, and synthetic peptides mimicking these sequences are good substrates for the same methyltransferases (Najbauer, J. et al. 1993).

SUMMARY

The invention relates to a transcriptional coactivator, Coactivator Associated arginine (R) Methyltransferase (CARM1).

One aspect of the invention includes CARM1 cDNA polynucleotides such as (SEQ ID NO: 1). Polynucleotides include those with sequences substantially equivalent to SEQ ID NO: 1, including fragments thereof. Polynucleotides of the present invention also include, but are not limited to, a polynucleotide complementary to the nucleotide sequence of SEQ ID NO: 1.

Polynucleotides according to the invention have numerous applications in a variety of techniques known to those skilled in the art of molecular biology. These techniques include use as hybridization probes, use as oligomers, i.e. primers for PCR, use for chromosome and gene mapping, use in the recombinant production of protein, and use in generation of antisense DNA or RNA, their chemical analogs and the like. For example, when the expression of an mRNA is largely restricted to a particular cell or tissue type, polynucleotides of the invention can be used as hybridization probes to detect the presence of the specific mRNA in the particular cell or tissue RNA using, e.g., in situ hybridization. The invention also includes vectors encoding the polynucleotides of the invention.

The invention also describes the deduced amino acid sequence of the CARM1 protein (SEQ ID NO: 2). The invention also describes isolated CARM1 proteins.

The polypeptides according to the invention can be used in a variety of procedures and methods that are currently applied to other proteins. For example, a polypeptide of the invention can be used to generate an antibody that specifically binds the polypeptide. The invention describes antibodies that specifically interact with the CARM1 protein or fragments thereof.

The polypeptides of the invention also act as methyltransferases of histones and other proteins and can therefore be used for the study of methylation processes in transcription and to methylate amino acid residues within histones and other proteins.

Methylated proteins produced by the methods of the invention can be used to identify demethylating enzymes. Methylated histones, for example, can be used to screen for demethylating enzymes.

The methods of the present invention further relate to the methods for detecting the presence of the polynucleotides or polypeptides of the invention in a sample. Such methods can, for example, be utilized as a prognostic indicator of diseases that involve CARM1 modified forms of CARM1, or altered expression of CARM1.

Methods are also provided for identifying proteins that interact with CARM1 as well as methods for screening of drugs that alter CARM1's interactions with other proteins.

Another aspect of the invention is to provide methods to screen for molecules that alter CARM1 methyltransferase activity.

BRIEF DESCRIPTION OF THE FIGURES

FIG. 1 shows a comparison of the region of highest homology between CARM1, three other mammalian protein arginine methyltransferases (Lin, W-J. et al. 1996; Tang, J. et al. (1998) *J. Biol. Chem.* 273:16935; Scott, H. S. et al. (1998) *Genomics* 48:330.) and one yeast protein arginine methyltransferase (Gary, J. D. et al. 1996); the sequences are shown, with dashes (–) representing the same amino acid as in CARM1 and dots (.) representing spaces inserted for optimum alignment. The location of a VLD-to-AAA mutation used in these studies is indicated.

FIG. 3 shows the binding in vitro of CARM1(SEQ ID NO: 2) and a CARM1 variant (SEQ ID NO: 3) to the C-terminal region of p160 coactivators.

FIG. 5 shows the enhancement by CARM1 of reporter gene activation by Gal4DBD-GRIP1$_c$. A) CV-1 cells in 6-well dishes (3.3 cm diameter well) were transiently transfected with 0.5 of μg pM.GRIP1$_c$ (coding for Gal4DBD-GRIP1$_c$ where GRIP1$_c$ is GRIP1 amino acids 1121–1462), 0.5 μg of GK1 reporter gene (luciferase gene controlled by Gal4 binding sites) (Webb, P. et al., (1998) *Mol. Endocrinol.* 12:1605), and 0–0.8 μg of pSG5.HA-CARM1, using Superfectin (Qiagen) according to manufacturer's protocol. Total DNA was adjusted to 2.0 μg per well with the appropriate amount of pSG5. Cell extracts were prepared approximately 48 h after transfection and assayed with Promega Luciferase Assay kit. Relative light units of luciferase activity presented are the mean and standard deviation of three transfected wells. B) CV-1 cells were transfected as in A with the indicated amount of pM.GRIP1, and zero or 0.5 μg of pSG5.HA-CARM1.

FIG. 6 shows the enhancement by CARM1 of reporter gene activation by nuclear receptors and the elimination of CARM1 coactivator function by the VLD-to-AAA mutation. (A) Transient transfection assays with CV-1 cells were performed as in FIG. 5 with 0.5 μg of GK1 reporter gene and 0.5 μg of each of the indicated vectors. (B) CV-1 cells were transiently transfected as in FIG. 5 with the following vectors, as indicated: 0.5 μg of nuclear receptor expression vector pSVAR$_0$ (Brinkmann, A. O. et al. (1989) *J. Steroid Biochem. Molec. Biol.* 34:307) expressing AR, pHE0 (Green, S. et al. (1988) *Nucleic Acids Res.* 16:369) expressing ER, orpCMX.hTRβ1 (Feng, W. et al. (1998) *Science* 280:1747) expressing TR; 0.5 μg of a luciferase reporter gene with an appropriate promoter, MMTV promoter for AR, or MMTV promoter with the native glucocorticoid response elements replaced by a single estrogen response element for ER or palindromic thyroid hormone response element for TR (Umesono, K. and R. M. Evans (1989) *Cell* 57:1139); 0.5 μg of pSG5.HA-GRIP1; and 0.5 μg of pSG5.HA-CARM1 or pSG5.HA-CARM1(VLD mutant). Transfection efficiency was monitored by using βgalactosidase activity expressed from 0.1 μg of co-transfected pCMV-βgal vector (Hong, H. et al. (1996) *Proc. Natl. Acad. Sci. USA* 93:4948–4952) as an internal control. After transfection, cells were grown in charcoal-treated serum; where indicated 20 nM hormone (H), i.e. dihydrotestosterone for AR, estradiol for ER, or triiodothyronine for TR, was included during the last 40 h of culture. The data is representative of three independent experiments.

FIG. 8 shows the histone methyltransferase activity of CARM1. CARM1 and PRMT1 have different protein methyltransferase substrate specificities. CARM1 methylates histone H3, whereas PRMT1 methylates histone H4. PRMT1 was also previously shown to methylate other proteins, including hnRNP A1, but had not previously been shown to methylate histone H4. (A,B) Calf thymus histones (Boehringer Mannheim) were incubated for 30 min at 30° C. in 32.5 μl reactions containing 20 mM Tris-Cl, 0.2 M NaCl, 4 mM EDTA, pH 8.0, 0.32 mg/ml individual histone (2a, 2b, 3, or 4) or 1.3 mg/ml mixed histone (M), 0.037 mg/ml GST-CARM1 or GST-PRMT1, and 7 μM S-adenosyl-L-[methyl-$^3$H]methionine (specific activity of 14.7 Ci/mmol). Reactions were stopped by addition of SDS-NuPAGE sample buffer (Novex), and 40% of each stopped reaction was then subjected to SDS-PAGE in 4–12% NuPAGE Bis-Tris gradient gels (Novex) using the Na-MES running buffer. Gels were stained with Coomassie Blue R-250 (A), and then subjected to fluorography (Chamberlin, M. (1978) *Anal. Biochem.* 98:132) for 12 h at −70° C. on sensitized Kodak XAR-5 film (B). Molecular weight markers (MW) are shown at left. Concentrations of GST fusion proteins were determined in comparison with bovine serum albumin standards (Sigma) by SDS polyacrylamide gel electrophoresis and Coomassie Blue staining; it was assumed that bovine serum albumin stained twice as intensely as most other proteins. Concentrations of histones and hnRNP A1 were determined by the method of Lowry (Lowry, O. H. et al. (1951) *J. Biol. Chem.* 193:265). (C) Methylation and electrophoresis were carried out as described above except that protein substrates were 2.7 mg/ml mixed histone (His), 0.083 mg/ml hnRNP-A1 (A1), or no substrate (−), and the concentrations of GST-CARM1, GST-CARM1 VLD mutant (VD), and GST-PRMT1, were 0.05, 0.02, and 0.03 mg/ml respectively. Two different preparations of the GST-CARM1 VLD mutant failed to show detectable activity towards any substrate. Recombinant human hnRNP A1 expressed in *E. coli* (Mayeda, A. A. R. and Krainer (1995) *Cell* 68:365) was kindly provided by Dr. A. Krainer (Cold Spring Harbor Laboratories, NY).

FIG. 10 shows that at low levels of nuclear receptor expression, the hormone dependent activity of the nuclear receptors depends almost entirely on the presence of three different coactivators, at least one of which is a protein methyltransferase. Several different combinations of three coactivators work: A) Orphan nuclear receptors ERR3 and ERR1, which require no ligand, are active without exogenously added coactivators when high levels of these nuclear receptors are expressed; but when low levels of these nuclear receptors are expressed (1 ng of expression plasmid in FIG. 10A), GRIP1+CARM1+PRMT1 is required for activity (226-fold over controls for ERR3 and 13.8-fold over controls for ERR1). Omission of any one of these coactivators almost completely eliminated activity. p160 coactivators other than GRIP1 could be substituted for GRIP1 with similar results. B) When high levels of estrogen receptor are expressed in CV-1 cells (using 100 ng of ER expression vector), the estrogen receptor alone is active, and the activity is enhanced by GRIP1 alone or GRIP1+one other coactivator (p300 or CARM1) (right side of panel). However, when low levels of estrogen are expressed (using 1–10 ng of ER expression vector) ER alone is almost inactive, and individual coactivators or combinations of any two coactivators cause little stimulation; activity is almost entirely dependent on the presence of GRIP1+CARM1+p300 (left side of panel).

DETAILED DESCRIPTION

Definitions

Figure 2:
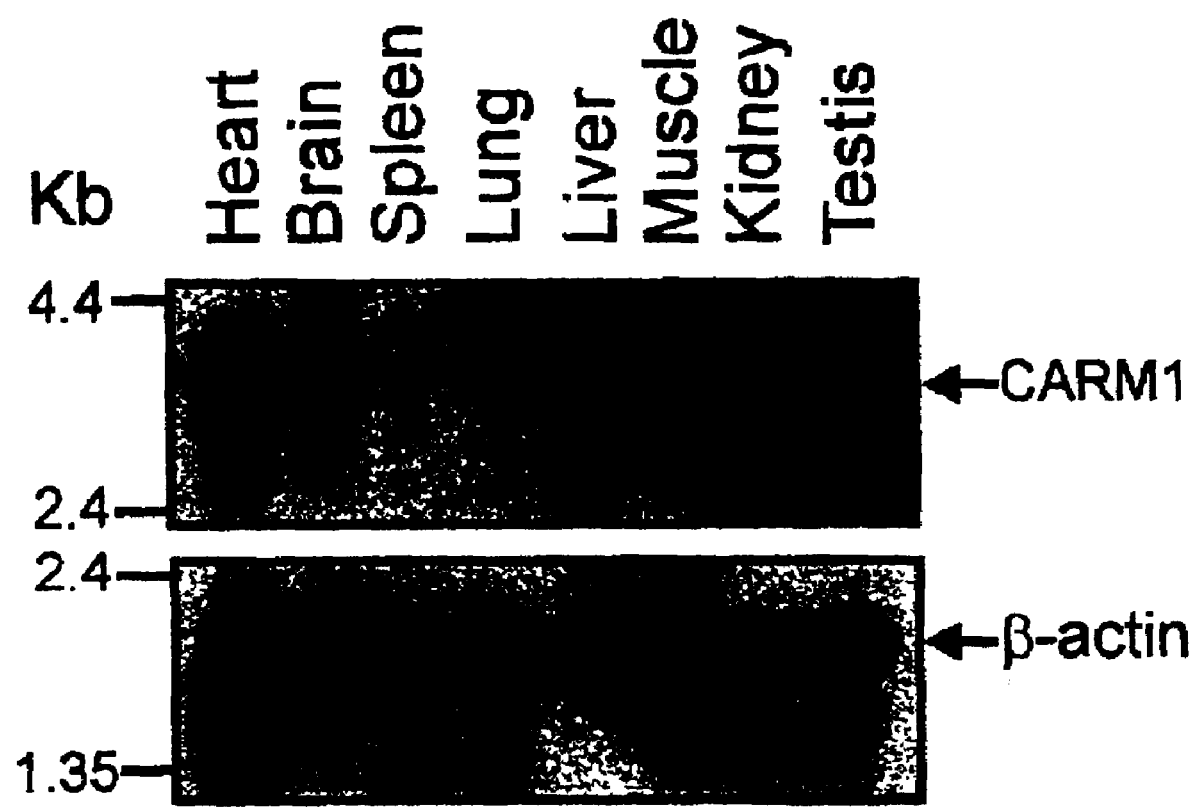
FIG. 2 shows the expression of CARM1 mRNA in various adult mouse tissues as examined by hybridizing a 0.6-kb BamHI cDNA fragment (representing CARM1 codons 3–198) to a multiple tissue northern blot (Clontech) as described previously (Hong, H. et al. 1997). Positions of RNA size markers are shown on the left.

The term "nucleotide sequence" refers to a heteropolymer of nucleotides or the sequence of nucleotides. One of skill in the art will readily discern from contextual cues which of the two definitions is appropriate. The terms "nucleic acid," "nucleic acid molecule" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment," "portion," or "segment" refer to a stretch of nucleotide residues which is long enough to use in polymerase chain reaction (PCR) or various hybridization procedures to identify or amplify identical or related parts of mRNA or DNA molecules.

"Oligonucleotides" or "nucleic acid probes" are prepared based on the polynucleotide sequences provided herein. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 3 kb, usually fewer than 1 kb. After appropriate testing to eliminate false positives, these probes may, for example, be used to determine whether specific mRNA molecules are present in a cell or tissue.

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989. *Molecular Cloning: A Laboratory Manual,* Cold Spring Harbor, N.Y.; or Ausubel, F. et al., 1989, *Current Protocols in Molecular Biology,* John Wiley & Sons, New York, both of which are incorporated herein by reference in their entirety.

The term "recombinant," when used herein to refer to a polypeptide or protein, means that a polypeptide or protein is derived from recombinant (e.g., microbial, mammalian, or insect-based) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli,* will be free of glycosylation modifications; polypeptides or proteins expressed in yeast may have a glycosylation pattern in general different from those expressed in mammalian cells.

The term "recombinant expression vector" refers to a plasmid or phage or virus or vector, for expressing a polypeptide from a polynucleotide sequence. An expression vector can comprise a transcriptional unit comprising an assembly of: 1) a genetic element or elements having a regulatory role in gene expression, for example, promoters or enhancers, 2) a structural or coding sequence which is transcribed into mRNA and translated into protein, and 3) appropriate transcription initiation and termination sequences. It may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also encompasses host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," or "ORF," means a series of nucleotide triplets coding for amino acids without any termination codons and is a sequence translatable into protein.

The term "active" refers to those forms of the polypeptide which retain a biologic and/or immunologic activity or activities of any naturally occurring polypeptide. An active polypeptide can possess one activity of a polypeptide, but not another, e.g., possess p160 binding activity but lack methyltransferase activity.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phoshorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as catalytic activity, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce polypeptide variants., Such variants can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges. A variant's catalytic efficiency can be diminished through deletion or non-conservative substitution of residues important for catalysis.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.20 or less). Such a sequence is said to have 80% sequence identity to the listed sequence. In one embodiment, a substantially equivalent, e.g., mutant, sequence of the invention varies from a listed sequence by no more than 20% (80% sequence identity); in a variation of this embodiment, by no more than 10% (90% sequence identity); and in a further variation of this embodiment, by no more than 5% (95% sequence identity). Substantially equivalent, e.g., mutant, amino acid sequences according to the invention generally have at least 80% sequence identity with a listed amino acid sequence.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites are well known in the art and may be introduced to optimize cloning: into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "purified" as used herein denotes that the indicated nucleic acid or polypeptide is present in the substantial absence of other biological macromolecules, e.g. polynucleotides, proteins, and the like. In one, embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "infection" refers to the introduction of nucleic acids into a suitable host cell by use of a virus or viral vector. The term "transformation" means introducing DNA into a suitable host cell so that the DNA is, replicable, either as an extrachromosomal element, or by chromosomal integration. The term "transfection" refers to the taking up of an expression vector by a suitable host cell, whether or not any coding sequences are in fact expressed.

Each of the above terms is meant to encompasses all that is described for each, unless the context dictates otherwise.

Polynucleotides and Nucleic Acids of the Invention

The invention provides polynucleotides substantially equivalent to SEQ ID NO: 1, which is the cDNA encoding the polypeptide sequence, SEQ ID NO: 2. The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

The polynucleotides of the invention also include nucleotide sequences that are substantially equivalent to the polynucleotides recited above. Polynucleotides according to the invention can have at least about 80%, more typically at least about 90%, and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA such as mRNA or an antisense RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) *Molecular Cloning: A Laboratory Manual*, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NO: 1, a representative fragment thereof, or a nucleotide sequence at least 98% identical to SEQ ID NO: 1, with a sequence from another murine isolate. An allelic variation is more typically at least, 99% identical to SEQ ID NO: 1 and even more typically 99.8% identical to SEQ ID NO: 1. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NO: 1 or a fragment thereof. The recombinant constructs of the present invention comprise a vector, such as a plasmid or viral vector, into which a nucleic acid having the sequence of SEQ ID NO: 1 or a fragment thereof is inserted, in a forward or reverse orientation. In the case of a vector comprising one of the ORFs of the present invention, the vector may further comprise regulatory sequence's including, for example, a promoter operably linked to the ORF. Large numbers of suitable vectors and promoters are known to those of skill in the art and are commercially available for generating the recombinant constructs of the present invention.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. In a preferred method, polynucleotides encoding the novel nucleic acids are changed via site-directed mutagenesis.

Use of Nucleic Acids as Probes

Another aspect of the subject invention is to provide for polypeptide-specific nucleic acid hybridization probes capable of hybridizing with naturally-occurring nucleotide sequences. The hybridization probes of the subject invention may be derived from the nucleotide sequence of SEQ ID NO: 1, fragments or complements thereof. Because the corresponding gene is only expressed in a limited number of tissues, a hybridization probe derived from SEQ ID NO: 1 can be used as an indicator of the presence of RNA of cell type of such a tissue in a sample as shown in Example 1.

Such probes may be of recombinant origin, may be chemically synthesized, or a mixture of both. The probe will comprise a discrete nucleotide sequence for the detection of identical sequences or a degenerate pool of possible sequences for identification of closely related genomic sequences. Other means for producing specific hybridization probes for nucleic acids include the cloning of nucleic acid sequences into vectors for the production of mRNA probes.

Hosts

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell or an insect cell, a lower eukaryotic host cell, such as a yeast cell, or, the host cell can be a prokaryotic cell, such as a bacterial cell. Introduction of the recombinant construct into the host cell can be effected by calcium phosphate transfection, DEAE, dextran mediated transfection, or electroporation (Davis, L., et al., *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of an appropriate promoter region.

Any host/vector system can be used to express one or more of the ORFs of the present invention. These include, but are not limited to, eukaryotic hosts such as HeLa cells, CV-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual,* Second Edition, Cold Spring Harbor, N.Y. (1989).

Regulation of Transcription

Polynucleotides of the invention and vectors capable of expressing these polynucleotides are useful for the regulation of transcription in cells.

Increased expression of CARM1 in cells enhances the function of nuclear receptor coactivators of the p160 family including GRIP1, SRC-1, and p/CIP. CARM1 expression in mammalian cells enhances the activity of full length GRIP1 or of the C-terminal domain of GRIP1 attached to the DNA binding domain of a heterologous protein. Increased expression of CARM1 in cells, in conjunction with increased expression of coactivators of the GRIP1 family, enhances the function of nuclear receptors. The enhancement by CARM1 is over and above that achieved by the increased expression of a GRIP1-type coactivator. Thus, CARM1 can serve as a coactivator for nuclear receptors.

The activity of other transcriptional activator proteins that rely on GRIP1-type coactivators will be enhanced by increased expression of CARM1. Examples of other transcriptional activator proteins that may use GRIP1-type coactivators are other nuclear receptors, AP1, and STATs (Glass C K et al. (1997) *Curr. Opin. Cell Biol.* 9:222–232; Kamei Y et al. (1996) *Cell* 85:403–414; Korzus E et al. (1998) *Science* 279:703–707; Yao T-P et al. (1996) *Proc. Natl. Acad. Sci. USA* 93:10626–10631).

CARM1 polynucleotides or polypeptides can also be used in conjunction with other transcriptional activating molecules to increase transcription of a nuclear receptor-dependent gene. In one embodiment, CARM1 is expressed simultaneously with a histone acetyl transferase (HAT). Transcription of a gene under the control of a nuclear receptor is synergistically enhanced by the presence of CARM1 and a HAT.

Gene Therapy

Polynucleotides of the present invention can also be used for gene therapy for the treatment of disorders which are mediated by CARM1, certain hormones, such as those that act as ligands for nuclear hormone receptors, or by nuclear hormone receptors. Such therapy achieves its therapeutic effect by introduction of the appropriate CARM1 polynucleotide (e.g., SEQ ID NO: 1) which contains a CARM1 gene (sense or antisense), into cells of subjects having the disorder to increase or decrease CARM1 activity in the subjects' cells. Delivery of sense or antisense CARM1 polynucleotide constructs can be achieved using a recombinant expression vector such as a chimeric virus or a colloidal dispersion system. An expression vector including the CARM1 polynucleotide sequence may be introduced to the subject's cells ex vivo after removing, for example, stem cells from a subject's bone marrow. The cells are then reintroduced into the subject, (e.g., into subject's bone marrow).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), Rous Sarcoma Virus (RSV), and gibbon ape leukemia virus (GaLV), which provides a broader host range than many of the murine viruses. A number of additional retroviral vectors can incorporate multiple genes. All of these vectors can transfer or incorporate a gene for a selectable marker so that transduced cells can be identified and selected for. By inserting a CARM1 sequence of interest into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome to target a specific retroviral vector containing the CARM1 sense, or antisense polynucleotide.

Since recombinant retroviral vectors usually are defective, they require assistance to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to PSI.2, PA317 and PA12, for example. These cell lines produce empty virions, since no genome is packaged. If a retroviral vector in which the packaging signal is intact, but the structural genes are replaced by other genes of interest is introduced into such cells, the vector will be packaged and vector virions produced.

Since CARM1 promotes the action of nuclear receptors, CARM1 or vectors expressing CARM1 may be useful as agonists to stimulate processes mediated by nuclear receptors. For example, glucocorticoids are used as anti-inflammatory agents. Gene therapy applications of CARM1 may enhance the anti-inflammatory effects of glucocorticoids and could thus enhance the glucocoticoids' therapeutic effectiveness or reduce the concentration of glucocorticoids required to provide the desired anti-inflammatory effects.

The CARM1 nucleotide and predicted amino acid sequence, combined with the functional domains of CARM1, can be used to design modified forms of CARM1 that lack the methyltransferase activity but retain the ability to bind GRIP1-type coactivators. For example, we have shown that mutations in the region of CARM1 that contains the methyltransferase activity produce such a modified CARM1 protein. Also, a fragment of CARM1 protein that contains the GRIP1-binding function but lacks the methyltransferase region will also have the same properties. Such forms of CARM1 have a "dominant negative" effect on nuclear receptor function; i.e., when expressed in cells, these dominant negative forms of CARM1 reduce the activity of nuclear receptors. This approach is effective in cells that naturally express CARM1 or a functionally equivalent protein from the native endogenous gene. The dominant negative variant of CARM1 interferes with the function of the endogenous CARM1 (or functionally equivalent protein) as follows: When nuclear receptors bind to a target gene, they recruit a GRIP1-type coactivator, which would normally recruit CARM1. However, if the dominant negative form of CARM1 is expressed in higher levels than the endogenous intact CARM1, then the dominant negative CARM1 is more likely to bind to GRIP1 instead of the endogenous active CARM1. The recruited dominant negative form of CARM1 fails to activate gene expression (since it has no methyltransferase), and also blocks the endogenous intact CARM1 protein from binding to GRIP1 and carrying out its function. Thus, the expression of the dominant negative CARM1 reduces the nuclear receptor's ability to activate gene expression by interfering with the function of endogenous CARM1. The same forms of CARM1 should have a dominant negative effect on any transcription factor whose function is normally enhanced by intact CARM1. We have demonstrated that a CARM1 mutant (CARM1 VLD mutant), in which the amino acids valine189, leucine190, and aspartic acid191 (V189A/L190A/D191A) have all been changed to alanine, lacks methyltransferase activity, lacks coactivator activity, and inhibits nuclear receptor function in conditions where GRIP1-type coactivators are limiting.

Examples of specific uses for such antagonistic reagents are in the treatment of breast cancer and prostate cancer. Most breast cancers, at least initially, rely on estrogen for growth; and most prostate cancers, at least initially, depend on androgens for growth. Since CARM1 promotes estrogen and androgen receptor action, antagonists of CARM1 or other methyltransferases may block or partially block the growth promoting effects of the hormones estrogen and androgen on these tumors. These antagonists may serve as effective chemotherapeutic agents, either when used alone or when used in combination with other types of treatments.

Polypeptides of the Invention

The isolated polypeptides of the invention include, but are not limited to, a polypeptide comprising the amino acid sequence of SEQ ID NO: 2 or fragments thereof.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The invention also provides a polypeptide including an amino acid sequence that is substantially equivalent to SEQ ID NO: 2. Polypeptides according to the invention can have at least about 80%, and more typically at least about 90%, and even more typically 95 sequence identity to SEQ ID NO: 2.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

Methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from cells which naturally produce the polypeptide or protein. One skilled in the art can readily follow known methods for isolating polypeptides and proteins to obtain one of the isolated polypeptides or proteins of the present invention. These include, but are not limited to, immunochromatography, HPLC, size-exclusion chromatography, ion-exchange chromatography, and immuno-affinity chromatography. See, e.g. Scopes, *Protein Purification: Principles and Practice*, Springer-Verlag (1994); Sambrook, et al., in *Molecular Cloning: A Laboratory Manual* (supra); Ausubel et al., *Current Protocols in Molecular Biology* (supra).

The polypeptides and proteins of the present invention can alternatively be purified from cells which have been altered to express the desired polypeptide or protein. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides.

The protein may also be produced by known conventional chemical synthesis. Methods for constructing the proteins of the present invention by synthetic means are known to those skilled in the art. For polypeptides more than about 100 amino acid residues, a number of smaller peptides will be chemically synthesized and ligated either chemically or enzymatically to provide the desired full-length polypeptide. The synthetically-constructed protein sequences, by virtue of sharing primary, secondary or tertiary structural and/or conformational characteristics with naturally occurring proteins may possess biological properties in common therewith. Thus, they may be employed as biologically active or immunological substitutes for natural, purified proteins in screening of therapeutic compounds and in immunological processes for the development of antibodies.

The proteins provided herein also include proteins characterized by amino acid sequences substantially equivalent to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are intended to be encompassed by the present invention.

The protein of the invention may also be expressed in a form that will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and Invitrogen (Carlsbad, Calif.), respectively. The protein also can be tagged with an epitope and subsequently purified by using a specific antibody directed to such epitope. One such epitope ("Flag") is commercially available from Kodak (New Haven, Conn.).

Our knowledge of CARM1 should make it possible to design and screen drugs that block the methyltransferase activity of CARM1. The CARM1 protein can in principle be used for X-ray crystallographic, or other structural studies, to determine the 3 dimensional structure of the active site (including the binding sites for S-adenosylmethionine and the protein substrate which accepts methyl groups) of the methyltransferase region of CARM1. Once determined, this structure can be used for rational drug design, to design drugs to block the substrate binding and activate sites of CARM1. These or randomly selected candidates can be screened using the methyltransferase activity assays we have developed.

There are other protein arginine methyltransferases related to CARM1 (Lin, W-J. et al. 1996; Gary, J. D. et al. 1996; Aletta, J. M. et al. 1998), and there maybe others which are unknown at this time. Some of these other protein arginine methyltransferases and possibly even some other types of protein methyltransferases (e.g., lysine methyltransferases and carboxyl methyltransferases (Aletta, J. M. et al. 1998) may also be involved in gene regulation by a mechanism similar to that of CARM1. Our knowledge of the CARM1 sequence and mechanism provides the tools to search for related genes and proteins and the knowledge to determine whether any of these other methyltransferases are involved in regulation of transcription.

Antibodies

Another aspect of the invention is an antibody that specifically binds the polypeptide of the invention. Such antibodies can be either monoclonal or polyclonal antibodies, as well as fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies that react specifically with the protein. Such antibodies may be obtained using either the entire protein or fragments thereof as an immunogen. The peptide immunogens additionally may contain a cysteine residue at the amino or carboxyl terminus, and are conjugated to a hapten such as keyhole limpet hemocyanin (KLH). Methods for synthesizing such peptides are known in the art, for example, as in R. P. Merrifield, *J. Amer. Chem. Soc.* 85, 2149–2154 (1963); J. L. Krstenansky, et al., *FEBS Lett.* 211, 10 (1987). Monoclonal antibodies binding to the protein of the invention may be useful diagnostic agents for the immunodetection of the protein. Neutralizing monoclonal antibodies binding to the protein may also be useful therapeutics for conditions associated with excess production or accumulation of the protein. In general, techniques for preparing polyclonal and monoclonal antibodies as well as hybridomas capable of producing the desired antibody are well known in the art (Campbell, A. M., *Monoclonal Antibodies Technology: Laboratory Techniques in Biochemistry and Molecular Biology*, Elsevier Science Publishers, Amsterdam, The Netherlands (1984); St. Groth et al., *J. Immunol.* 35:1–21(1990); Kohler and Milstein, *Nature* 256:495–497 (1975)). Other useful techniques include the trioma technique and the human B-cell hybridoma technique (Kozbor et al., *Immunology Today* 4:72 (1983); Cole et al., in *Monoclonal Antibodies and Cancer Therapy*, Alan R. Liss, Inc. (1985), pp. 77–96).

Any animal (rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered with an adjuvant to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al, *Exp. Cell Research,* 175: 109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, etc. Procedures for accomplishing such labeling are well-known in the art, for example, see Sternberger, L. A. et al., *J. Histochem. Cytochem.* 18:315 (1970); Bayer, E. A. et al., *Meth. Enzym.* 62:308 (1979); Engval, E. et al., *Immunol.* 109:129 (1972); Goding, J. W. *J. Immunol. Meth.* 13:215 (1976).

In diagnostic uses, it is possible that some medical conditions may derive from abnormal forms or levels of expression of CARM1 or other methyltransferases. Thus, nucleic acid and antibody reagents derived from CARM1 or other methyltransferases may be used to screen humans for such abnormalities. Similarly, there may be different alleles of CARM1 or other methyltransferases that predispose carriers to be more susceptible to specific drugs or diseases. The CARM1 reagents can be used to define such allelic variations and subsequently to screen for them.

Antibodies of the invention can also be generated that specifically recognize substrates that have been methylated by CARM1. For example, CARM1 methylates residues arg2, arg17 and arg26 of histone H3. Antibodies to peptides containing methylated arginines at these, or other positions of CARM1 methylation, are useful for studying the role of methylation in gene expression.

Methyltransferase Activity

CARM1 can transfer one or more methyl groups from S-adenosylmethionine to an arginine residue in proteins and in synthetic peptides. Appropriate substrate proteins include histones. CARM1 can transfer methyl groups from S-adenosylmethionine to one or more arginine residues in histone H3, producing monomethyl and asymmetrically dimethylated $N^G,N^G$-dimethylarginine residues in histone H3. The CARM1 VLD (SEQ ID NO:3) mutant lacks methyltransferase activity for both histone H3 and the synthetic peptide substrates and lacks coactivator activity.

Substrates of CARM1

While the identity of additional proteins (other than histone H3) that CARM1 methylates remains unknown, we have established a procedure for identifying proteins that are methylated by CARM1, by incubating candidate substrate proteins or protein fractions or extracts with recombinant CARM1 and S-adenosylmethionine and then analyzing the products by chromatography or electrophoresis. The purified protein can be sequenced to learn its identity. The yeast two hybrid system, used to discover CARM1, also should be useful for defining proteins that bind to CARM1 methyltransferase and thus are possible substrates. Once identified, these methylation substrates of CARM1 should be useful as reagents for studying the role and mechanism of methylation in gene regulation. They also serve as additional sites of intervention for blocking or enhancing gene expression. This is accomplished by increasing the expression of the protein substrate or by reducing expression of the protein substrate, for example by using antisense techniques or by expressing altered forms of the protein substrate which have a dominant negative effect and thus block the function of the endogenous native protein substrate.

Because protein methylation is involved in regulation of gene transcription, a mechanism for demethylation of the same proteins likely exists. Histone H3 is a substrate for CARM1, and we have described methods for identifying other protein substrates of CARM1 above. These methylated proteins can serve as the basis for identifying demethylating enzymes. In such a method, a methylated protein preparation is incubated with cell extracts, fractions of cell extracts or with candidate proteins. Demethylation can be monitored by release of radioactivity if the methylated protein is prepared with radioactively labeled S-adenosyl-methionine. Demethylation can also be monitored by chromatographic changes, using techniques such as ion-exchange chromatography; by mass spectrometry; by spectroscopic techniques such as fluorescence spectropscopy; or by immunoassays with antibodies raised against the methylated or non-methylated forms of the protein. Once identified, these demethylating enzymes can be used as the basis for developing reagents to enhance or block demethylation. Blocking or enhancing demethylation should have the opposite effect from blocking or enhancing methylation by CARM1.

Screening of CARM1 Inhibitors

Inhibitors of CARM1 can be discovered using the methods of the invention that act through a variety of mechanisms. In one embodiment, molecules are screened for their ability to inhibit CARM1 methyltransferase activity. Methyltransferase activity can be determined using any of the assays described herein, or other suitable biochemical assays. For example, in one embodiment a substrate protein, such as histone H3 is incubated with a candidate inhibitor molecule or pool of molecules along with CARM1 (SEQ ID NO: 2) and radioactively labeled S-adenosylmethionine. The degree of radioactive labeling of the target histone is measured by separating the labeled protein from the free S-adenosylmethionine. Separation may be effected by chromatography or by using a low molecular weight cut-off membrane, through which the free S-adenosylmethionine passes, but the labeled protein is retarded. The activity of CARM1 is then compared in the presence and absence of the candidate inhibitor.

CARM1 inhibitors can also be discovered that prevent interaction of CARM1 with a coactivator such as GRIP1. The disclosed two-hybrid assays for measuring the binding interaction between coactivators and CARM1 are also suitable for use as a screening system to identify compounds that can lock binding of CARM1 to GRIP1-type coactivators.

In one embodiment, CARM1 (SEQ ID NO: 1) or a fragment thereof, is expressed in a host cell as a fusion with either a DNA binding domain (DBD) or with a transcriptional activation domain (AD). DNA binding domains are well known in the art, and can be chosen from any DNA binding protein or transcription factor. In one embodiment, CARM1 is expressed fused with the DNA binding domain of Gal4. In another embodiment, CARM1 is expressed instead fused to a transcriptional activation domain from Gal4.

A GRIP1-type coactivator, or a fragment thereof, is expressed as a fusion with either a DNA binding domain or with a transcriptional activation domain, but not with the domain type chosen for CARM1. If CARM1 is fused with a DNA binding domain, then the GRIP1-type coactivator domain must be fused with a transcriptional activating domain.

In such a method, a reporter, gene construct is also provided. The reporter gene construct comprises a reporter gene and a promoter region. Reporter genes encode a protein that can be directly observed or can be indirectly observed through an enzymatic activity or through immunogenic detection methods. Directly observable proteins can be fluorescent proteins, such as the green fluorescent protein (GFP) of *Aequorea*. Indirectly observable proteins commonly possess an enzymatic activity capable of affecting a chromogenic or fluorogenic change in a specific substrate. Such proteins include β-lactamase, luciferase and β-galactosidase. Reporter gene expression can also be monitored with antibodies directed towards the gene product, or by measuring the RNA levels produced.

In the two hybrid system, the interaction of CARM1-AD hybrid protein with the GRIP1-DBD hybrid protein leads to the expression of the reporter gene, and thus, the expression of the reporter gene serves as an indication that CARM1 and GRIP1 can bind to each other.

Upon consideration of the present disclosure, one of skill in the art will appreciate that many other embodiments and variations may be made in the scope of the present invention. Accordingly, it is intended that the broader aspects of the present invention not be limited to the disclosure of the following examples, but rather only to the scope of the appended claims.

EXAMPLE 1

Isolation of Murine CARM1 cDNA

A 3.2-kb partial CARM1 cDNA clone with an open reading frame of 606 amino acids (CARM1(3–608)), followed by a 1.4 kb 3'-untranslated region and a poly A sequence, was isolated from a mouse 17-day embryo library by using the yeast two-hybrid system as described previously (Hong, H. et al. 1996). The EcoRI library (Clontech) was in vector pGAD 10 which has a leu2 marker gene; the bait was GRIP1c (GRIP (1122–1462)) in vector pGBT9 (Clontech) which has a trp1 marker gene. Further screening of a lambda phage library of mouse 11-day embryo cDNA clones (Stratagene) identified additional 5'-sequences and allowed construction of a putative full length coding region for CARM1 (608 amino acids). Amino acids 143–457 of CARM1 share 30% identity with hPRMT1 and yODP1. A clone coding for a C-terminal fragment of α-actinin was isolated in the same yeast two hybrid screen with pGBT9.GRIP1$_c$.

A BLAST search of the GenBank database (Altschul, S. F. et al. (1990) *J. Mol. Biol.* 215:403–410) indicated that this coding region represents a novel protein, whose central region shares extensive homology with a family of proteins with arginine-specific protein methyltransferase activity (FIG. 1). We therefore named the new protein Coactivator Associated arginine (R) Methyltransferase 1 (CARM1). RNA blot analysis indicated that the CARM1 cDNA represents a 3.8-kb mRNA which is expressed widely, but not evenly, in adult mouse tissues including in heart, brain, liver, kidney, and testis; testis also contains a homologous 4.1-kb RNA species (FIG. 2). Lower expression was observed in spleen, lung, and skeletal muscle. Northern blot analysis was performed as shown in FIG. 2 with a 0.6-kb BamHI cDNA fragment (representing CARM1 codons 3–198) and with RNA from multiple tissues as described previously (Hong et al. 1997).

EXAMPLE 2

Construction of Plasmids

Mammalian cell expression vector: pSG5.HA was constructed by inserting a synthetic sequence coding for a translation start signal, HA tag, EcoRI site, and XhoI site into the EcoRI-BamHI site of pSG5 (Stratagene), which has SV40 and T7 promoters. The original EcoRI site is destroyed by this insertion, but the BamHI site is preserved, leaving a multiple cloning site after the HA tag containing EcoRI, XhoI, BamHI, and BglII sites. The following protein coding regions were cloned into pSG5.HA, in frame with the HA tag, using the indicated insertion sites: GRIP1 (5–1462) (full length) and CARM1 (3–608) (full length) at the EcoRI site; GRIP1 (5–765) at the EcoRI-XhoI site; GRIP1 (730–1121) and GRIP1 (1121–1462) were EcoRI-SalI fragments inserted at the EcoRI-XhoI site; SRC-1a (1–1441) (full length) was a SmaI-SalI fragment inserted at the EcoRI site, which was blunted by filling with Klenow polymerase, and the XhoI site. Expression vector for Gal4DBD-GRIP1$_c$ was constructed by inserting an EcoRI-BglII fragment coding for GRIP1 (1122–1462) into pM (Clontech). Vectors for GST fusion proteins were constructed in pGEX-4T1 (Pharmacia): for GST-CARM1 the original 3.2-kb EcoRI fragment from pGAD10.CARM1 was inserted; for GST-GRIP1c (amino acids 1122–1462) a EcoRI-SalI fragment was inserted. Yeast expression vectors for Gal4DBD fused to various GRIP1 fragments were constructed by inserting EcoRI-SalI fragments into pGBT9. The GRIP1$_c$Δ19 and CARM1 VLD mutations were engineered with the Promega Gene Editor Kit. Constructions of all the above plasmids was described previously (Chen, D. et al. (1999) *Science* 284:2174–2177).

EXAMPLE 3

Binding Interactions of CARM1

This example demonstrates that CARM1 interacts with GRIP1. The binding of GRIP1$_c$ to CARM1 observed in the yeast two-hybrid system was confirmed in vitro, by incubating glutathione S-transferase (GST) fusion proteins attached to glutathione agarose beads with labeled proteins or protein fragments translated in vitro. GST-CARM1 bound GRIP1$_c$ (amino acids 1122–1462) but not protein fragments representing GRIP1 amino acids 5–765 or 730–1121 (FIG. 3A). Conversely, GST-GRIP1$_c$ bound CARM1 and the VLD to AAA mutant of CARM1 (FIG. 3B). GST-CARM1 not only bound GRIP1 but also the other two members of the p160 coactivator family, SRC-1a and ACTR (FIG. 3A). Thus, FIG. 3 shows the binding of CARM1 to the C-terminal region of p160 coactivators. GST fusion proteins of CARM1 or the indicated GRIP1 fragments produced in *E. coli* strain BL21 (Stratagene), were bound to glutathione-agarose beads and incubated with labeled full length CARM1 or p160 coactivators or GRIP1 fragments translated in vitro from vector pSG5.HA-CARM1, pSG5.HA-GRIP1, pSG5.HA-SRC-1a (Chen, D. et al. 1999), or pCMX.ACTR (Chen et al.

1997); bound labeled proteins were eluted and analyzed by SDS polyacrylamide gel electrophoresis as described previously (Hong et al. 1996). A mutant form of CARM1 with the triple amino acid substitution (VLD changed to AAA) shown in FIG. 1 still retains the ability to bind to the C-terminal fragment of GRIP1.

Figure 4:
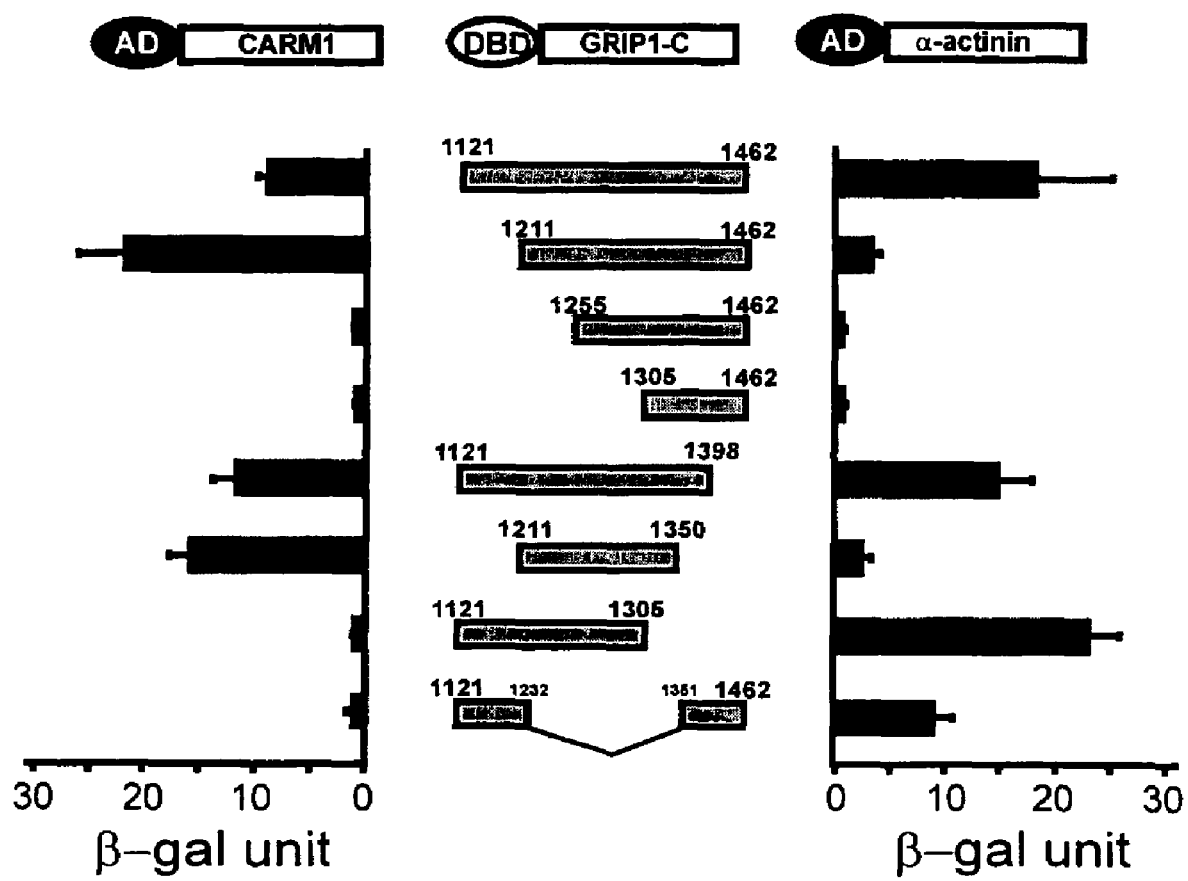
FIG. 4 shows binding of CARM1 to GRIP1 in vivo, i.e. in living yeast. Sub-fragments of the GRIP1 C-terminal domain (GRIP1$_c$), fused with the Gal4DBD, were tested in the yeast two-hybrid system as described previously (Ding, X. F. et al. (1998) *Mol. Endocrinol.* 12:302) for binding to CARM1 or to α-actinin, fused to Gal4AD. β-galactosidase (β-gal) activity indicates interaction between the two hybrid proteins.

The binding site for CARM1 in GRIP1$_c$ was further mapped by using the yeast two hybrid system. When GRIP1$_c$ was bisected between amino acids 1210 and 1211, the N-terminal fragment fails to bind CARM1, while the C-terminal fragment retains binding activity; thus GRIP 1211–1462 is sufficient for CARM1 binding while amino acids 1121–1210 are neither necessary nor sufficient (FIG. 4). When GRIP1$_c$ was bisected between amino acids 1305 and 1306, neither fragment bound CARM1, indicating that sequences near this boundary were important for CARM1 binding. This conclusion was supported by the finding that deletion of amino acids 1291–1309 (GRIP1$_c$Δ19 mutant), which are highly conserved among p160 proteins (Anzick, S. L. et al. 1997), eliminate CARM1 binding. The smallest GRIP1 fragment that binds to CARM1 is the fragment from 1211–1350. Controls with α-actinin, another protein found to bind GRIP1$_c$ in the yeast two hybrid screen, had a different pattern of binding to the GRIP1 fragments and provided positive and negative controls. We conclude that CARM1 binds to the C-terminal region of GRIP1 defined by amino acids 1211–1350 and that a highly conserved stretch of 19 amino acids (1291–1309) is important for CARM1 binding.

EXAMPLE 4

Enhancement of GRIP1 and NR Function by Secondary Coactivator CARM1

This example demonstrates that CARM1 expression in mammalian cells enhances the transcriptional activation activity of GRIP1$_c$ fused to the DBD of Gal4 protein. In transient transfections of CV-1 cells, Gal4DBD-GRIP1$_c$ weakly activates expression of a reporter gene with a promoter containing Gal4 binding sites; co-expression of CARM1 enhances reporter gene activity in a dose-dependent manner and provides a maximum stimulation of more than 10-fold (FIG. 5). CARM1 expression has little if any effect on the activity of Gal4DBD alone (FIG. 6A). CARM1 also enhances the activity of full length GRIP1 fused to Gal4DBD.

Figure 7:
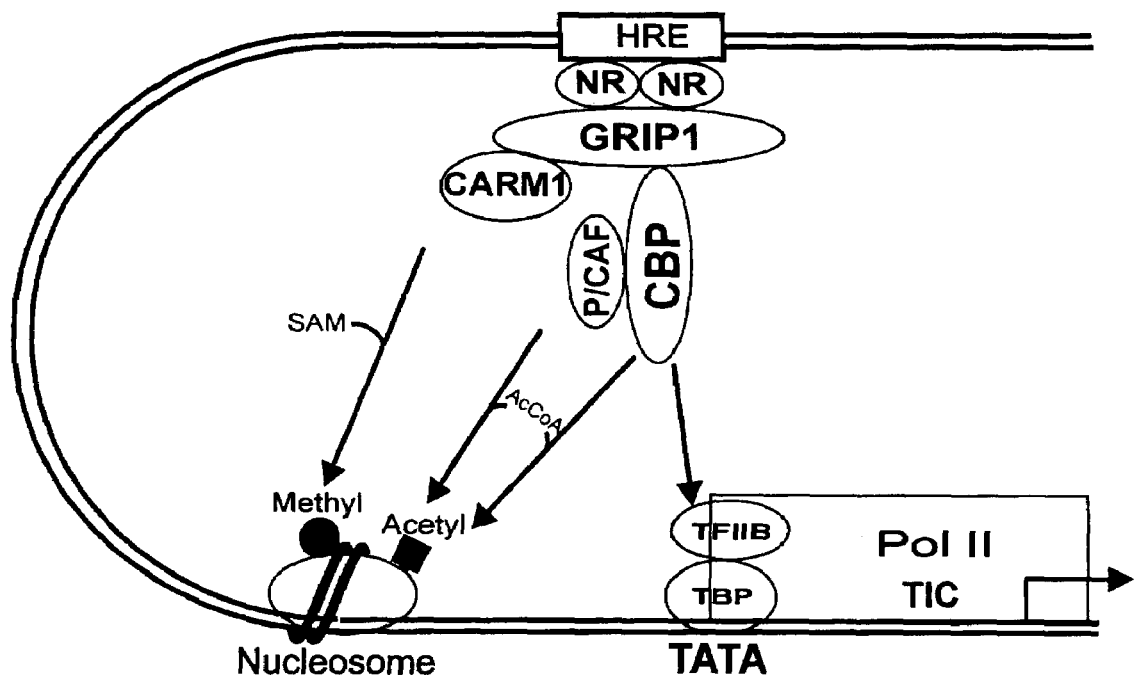
FIG. 7 shows a model for primary and secondary coactivators of nuclear receptors (NR). Nuclear receptor dimers bind directly to the hormone response element (HRE) and activate transcription by recruiting coactivators, which open chromatin structure (signified by nucleosome) and recruit a transcription initiation complex (TIC), composed of RNA polymerase II (Pol II), basal transcription factors such as TBP and TFIIB, and a large complex of accessory proteins (Chang, M. and J. A. Jaehning (1997) *Nucleic Acids Res.* 25:4861). GRIP1 and other p160 family members serve as primary coactivators in this case, binding directly to the NRs. CBP, p/CAF, and CARM1 are recruited by the primary coactivators and thus serve as secondary coactivators. Some coactivators (e.g. CBP) may help to recruit the TIC through direct interactions with basal transcription factors. Some coactivators (e.g. CBP and p/CAF) can acetylate histones, using acetyl-CoA (AcCoA). We propose that CARM1's coactivator activity is due to its ability to methylate histones or other proteins in chromatin or the transcription initiation complex, using S-adenosylmethionine (SAM) as methyl donor.

CARM1 also enhances GRIP1's coactivator function for nuclear receptors (NR). When the androgen receptor, estrogen receptor, and thyroid hormone receptor are expressed in CV-1 cells by transient transfection, their abilities to activate transcription of a reporter gene carrying appropriate hormone response elements in the promoter are hormone dependent (FIG. 6B, lanes a & b). Co-expression of GRIP1 from a co-transfected plasmid causes a 2 to 27-fold enhancement of reporter gene expression by the hormone-activated NR (lane d). These activities are enhanced 2 to 4-fold more by co-expression of CARM1 with the NR and GRIP1 (lane e). However, in the absence of exogenous GRIP1, CARM1 has little or no effect on the activity of the NR (lane c). Co-expression of NR, GRIP1, and CARM1 in the absence of hormone produces extremely low reporter gene activities equivalent to those seen with NR alone in the absence of hormone (lane f). A similar enhancement of NR function by CARM1 is observed when SRC-1a or ACTR (two other GRIP1 related coactivators) is substituted for GRIP1 in a similar experiment. The fact that CARM1's ability to enhance NR activity depends on co-expression of exogenous GRIP1 is consistent with a model whereby CARM1 interacts with NRs indirectly, through a p160 coactivator, rather than directly (FIG. 7). It also suggests that in the transient transfection assays, the expression of exogenous NRs renders the levels of endogenous p160 coactivators limiting, so that the effects of exogenous CARM1 expression can only be observed when additional p160 coactivators are also expressed. We conclude that CARM1 acts as a secondary coactivator for NRs by binding to and mediating or enhancing the activity of the p160 primary coactivators.

EXAMPLE 5

Histone Methyltransferase Activity of CARM1

This example shows that CARM1 is a protein arginine methyltransferase. The homology between CARM1 and arginine-specific protein methyltransferases includes sequences that are highly conserved throughout the family and are believed to be important for methyltransferase activity (FIG. 1). We compared the methyltransferase activities of GST fusion proteins of CARM1 and a related mammalian enzyme, Protein arginine (R) MethylTransferase 1 (PRMT1) (Lin, W-J. et al. 1996), for various substrates using S-adenosylmethionine labeled in the donor methyl group. Mixed histones are good substrates for both enzymes (FIG. 8). Gel electrophoresis and autoradiography of the methylated histone products, and tests with purified individual histone species, indicate that CARM1 methylates histones H3 and H2a, while PRMT1 methylates histones H4 and H2a (FIG. 8B). Both enzymes methylate histone 2a in the absence of other histones but not in the histone mixture, suggesting that hetero-oligomerization of the histones may render histone 2a inaccessible to methylation (FIG. 8B). The positions of the small amounts of labeled products in the histone H2b lanes for CARM1 and PRMT1 suggest that these products are minor amounts of H3 and H4 contaminating the H2b preparation. The specific activities of CARM1 and PRMT1 with the mixed histone substrate are very similar (Table 1). Our result for PRMT1 is different from one in a previous report (Gary and Clarke 1998), that PRMT1 methylates histone H2b but none of the other core histones. RNA binding protein hnRNPA1 is a good substrate for PRMT1, as shown previously (Lin W-J, et al. 1996), but is not methylated by CARM1 (FIG. 8C). Both enzymes methylate the glycine-rich R1 peptide substrate (SEQ ID NO: 4: GGFGGRGGFG-NH$_2$), which was previously shown to be a good substrate for PRMT1 and other protein arginine methyltransferases (Lin, W-J. et al. 1996; Najbauer, J. et al. 1993). However, this peptide is a relatively poor substrate for CARM1; the specific activity of GST-PRMT1 for the R1 peptide is approximately 100 times higher than that of GST-CARM1 (Table 1). CARM1 fails to methylate the same peptide with lysine substituted for the arginine residue, demonstrating its specificity for arginine.

TABLE 1

Relative methyltransferase activities of GST-CARM1 and GST-PRMT1. Methyltransferase reactions (50 µl) were carried out as described in FIG. 8 at enzyme concentrations of 0.03–0.05 mg/ml. Reactions were stopped by addition of 25 µl of 1.5% (v/v) trifluoroacetic acid (TFA), 15% (v/v) acetonitrile in water and subjected to reversed-phase HPLC as described (Najbauer et al. 1993) to separate the substrate from unreacted S-adenosylmethionine. For the histone methylation, TFA in the HPLC solvents was increased to 0.3% (v/v) and the gradient was modified to accommodate the more retentive behavior of the histones.

| Substrate | Methyltransferase specific activity (pmol/min/mg) | |
| --- | --- | --- |
|  | GST-CARM1 | GST-PRMT1 |
| R1 peptide (120 µM) SEQ ID NO: 4 GGFGGRGGFG-NH$_2$ | 21.6–54.5[a] | 3,070 |
| K1 peptide (120 µM) SEQ ID NO: 5 GGFGGKGGFG-NH$_2$ | 0.7 | not determined |
| mixed histones (2.7 mg/ml) (calf thymus) | 971 | 1,180 |

[a]Result of two separate determinations using different preparations of GST-CARM1.

EXAMPLE 6

Identification of the Methylated Amino Acids Produced in Histone H3 by CARM1

Histone H3 was incubated for 60 min at 30° C. in a 100 µl methylation reaction as described in FIG. 8, containing 0.024 mg/ml GST-CARM1 and 0.63 mg/ml H3. The reaction was stopped with 25 µl of 3% (v/v) trifluoroacetic acid (TFA), 15% (v/v) acetonitrile, and 100 µl was injected into a 3 cm×4.6 mm RP-300 reversed-phase guard column (Perkin Elmer-Brownlee) equilibrated with 80% solvent A (0.3% TFA in water) and 20% solvent B (0.3% TFA in acetonitrile). Methylated H3 was separated from unreacted S-adenosylmethionine using a gradient of 20–80% solvent B over 5 min at a flow rate of 1.0 ml/min. H3 eluted as a broad complex peak detected by monitoring absorbance at 214 nm. The H3 pool was reduced to dryness in a vacuum centrifuge and then subjected to acid hydrolysis in 6 N HCl at 112° C. for 20 h. A portion of the hydrolyzate was derivatized with o-phthaldialdehyde (Jones, B. N., *Methods of Protein Microcharacterization*, J. E. Shively, Ed. (Humana Press, Clifton, N.J., 1986), p. 337) and injected into a 10 cm×4.6 mm Rainin Microsorb 800PA-C3 column fitted with a guard module and equilibrated with 95% solvent A (50 mM Na-acetate, pH 5.9: methanol:tetrahydrofuran, 79:20:1) and 5% solvent B (50 mM Na-acetate, pH 5.9:methanol, 20:80) Elution was carried out with a linear gradient of 5–40% B over 20 min at a flow rate of 1.0 m/min. Radioactivity in the fractions was determined by liquid scintillation counting, and peak identity was determined by comparison to derivatized standards including the three major forms of methylarginine and methyllysine. In addition, another portion of the acid hydrolyzate was subjected to ascending chromatography on thin layers on cellulose using pyridine:acetone: ammonium hydroxide:water (15:9:1.5:6) (Desrosiers, R. and Tanguay (1988) *J. Biol. Chem.* 263:4686). Radioactive spots corresponding to the positions of the three forms of methylarginine (which all separated from each other) were removed by scraping the chromatogram, and quantified by liquid scintillation counting. Sources of standards: monomethyl-L-arginine and trimethyl-L-lysine, Calbiochem; N,N'-dimethyl-L-arginine and monomethyl-L-lysine, Sigma; N,N-dimethyl-L-arginine, Chemical Dynamics, Corp.; dimethyl-L-lysine, Serva.

When histone H3 is methylated by CARM1, hydrolyzed to amino acids, derivatized, and analyzed by high performance liquid chromatography (as described above), all of the radioactivity from histone H3 co-elutes in a single peak along with the derivatized standards of $N^G$-monomethylarginine and $N^G,N^G$dimethylarginine (which did not separate from each other). The radioactive peak was well separated from standards of $N^G,N'^G$-dimethylarginine, $N^\epsilon$-monomethyllysine, $N^\epsilon$-dimethyllysine, and $N^\epsilon$-trimethyllysine. On thin layer chromatography of the hydrolyzate, approximately 70% of the radiolabel migrated with $N^G,N^G$-dimethylarginine (asymmetrically dimethylated in the guanidino group) and the remaining 30% with $N^G$-monomethylarginine. In confirmation of the HPLC results, no significant label migrated with $N^G,N'^G$-dimethylarginine (symmetrically dimethylated in the guanidino group). Methylation of mixed histones by PRMT1 was previously shown to produce the same types of methylated arginine residues (Gary and Clark 1998). However, while they produce the same types of methylated arginine residues, CARM1 and PRMT1 have dramatically different protein substrate specificities (FIG. 8 and Table 1). Histone H4, nucleolin, fibrillarin and hnRNPA1, as well as the peptide substrate, all have arginine-containing glycine-rich motifs, whereas histone H3 does not (Najbauer, J. et al. 1993; Lin, W-J. et al. 1996; Genbank Accession Numbers, for calf thymus histone H3, 70749, and for histone H4, 70762). Thus, it appears that PRMT1 prefers to methylate arginines found in the glycine-rich motifs, whereas CARM1 targets a different arginine-containing motif in proteins.

EXAMPLE 7

Sites of CARM1 Methylation of Histone H3

CARM1 methylated the following residues of histone H3, as determined by mass spectrometry analysis: arg2 (minor), arg17 (major), arg26 (major), and one or more of the 4 arginine residues within the histone H3 peptide region comprising residues 128–134. N-terminal sequencing of histone H3 labeled by CARM1-mediated methylation confirmed that within the first 20 amino acids of histone H3, arg2 was a minor methylation site, arg17 was a major methylation site, and arg8 was not methylated (those are the only three arg residues within the first 20 amino acids of H3). The sequencing run was only able to analyze the first 20 amino acids from the N-terminus.

EXAMPLE 8

The Role of Methyltransferase Activity in Transcription

This example show that CARM1's methyltransferase activity is necessary for its activity as a coactivator of transcription. We made a mutation in the CARM1 coding sequences that resulted in replacement of three amino acids, valine 189, leucine 190, and aspartic acid 191, with alanines. This VLD sequence is located in the region that is most highly conserved among different members of the protein arginine methyltransferase family (FIG. 1) and is believed to be important for S-adenosylmethionine binding and thus for methyltransferase activity (Lin, W-J. et al. (1996) *J. Biol. Chem.* 271:15034–15044). This mutation completely eliminates the ability of the GST-CARM1 fusion protein to methylate mixed histones (FIG. 8C) and peptide substrate R1 (SEQ ID NO:4). The same mutation essentially eliminates CARM1's ability to enhance transcriptional activation by a Gal4DBD-GRIP1$_c$ fusion protein (FIG. 6A) or by the estrogen receptor (FIG. 6B). Immunoblots of transfected COS7 cell extracts indicated that both wild type and mutant CARM1 were expressed at similar levels. The VLD mutant retains the ability to bind the C-terminal region of GRIP1 (FIG. 3B). The correlated loss of the methyltransferase activity and coactivator activity of CARM1 indicates that methyltransferase activity is important for CARM1's coactivator function.

EXAMPLE 9

Figure 9:
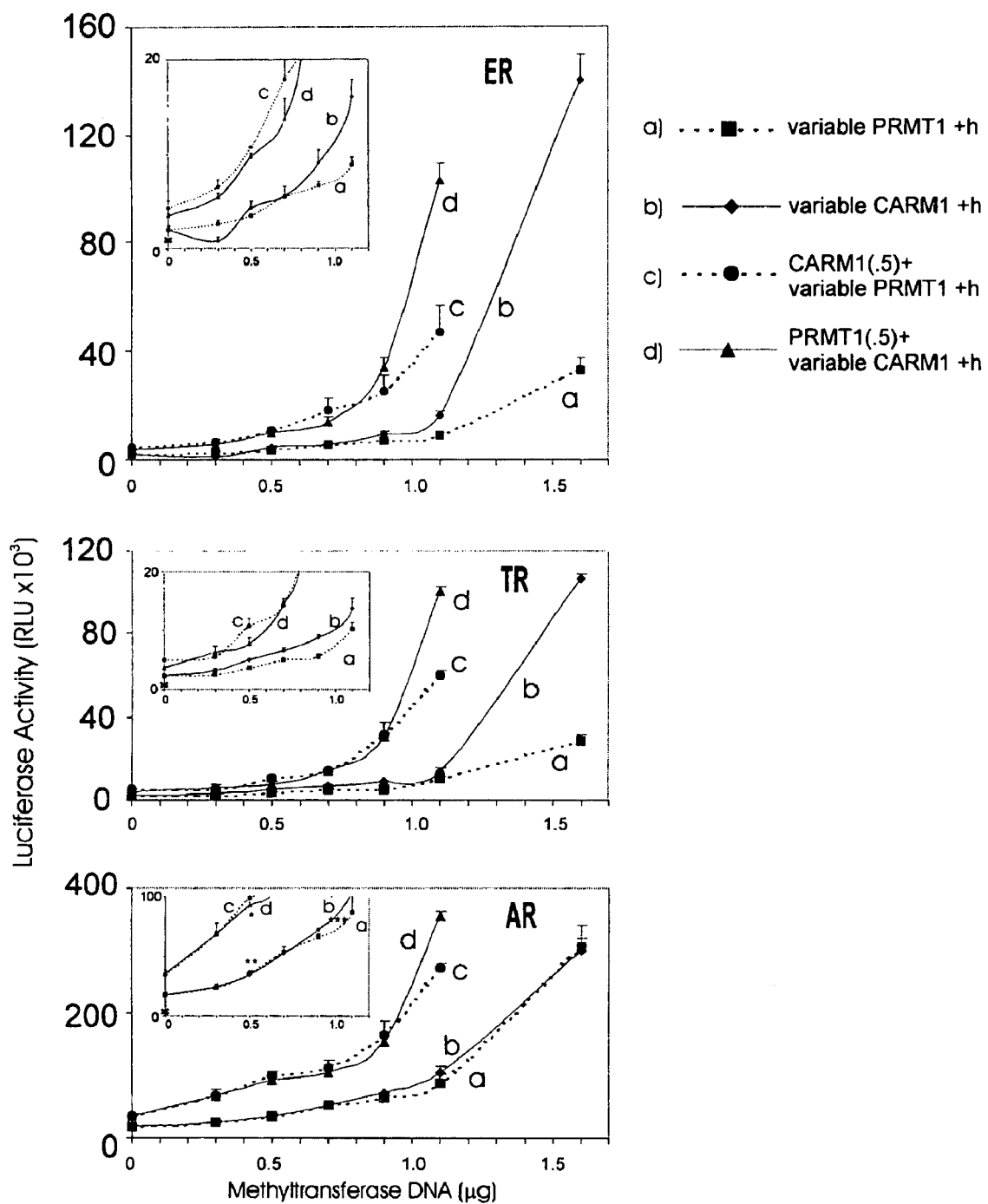
FIG. 9 shows that PRMT1 can also serve as a coactivator for nuclear receptors. Furthermore, CARM1 and PRMT1 act cooperatively as enhancers of nuclear receptor function, i.e. the two together are at least as effective or more effective than the sum of their individual activities. Transient transfections were performed as in FIG. 5. CV-1 cells were transfected with the following plasmids: expression vector for nuclear receptor (0.1 μg pSVAR$_0$ for androgen receptor [AR], 0.001 μg of pCMX.TRβ1 for thyroid receptor [TR], or 0.001 μg of pHE0 for estrogen receptor [ER]), 0.25 μg of reporter gene for each nuclear receptor as described in FIG. 6B, 0.25 μg of pSG5.HA-GRIP1, and the indicated amount of plasmids encoding CARM1 or PRMT1.
Figure 11:
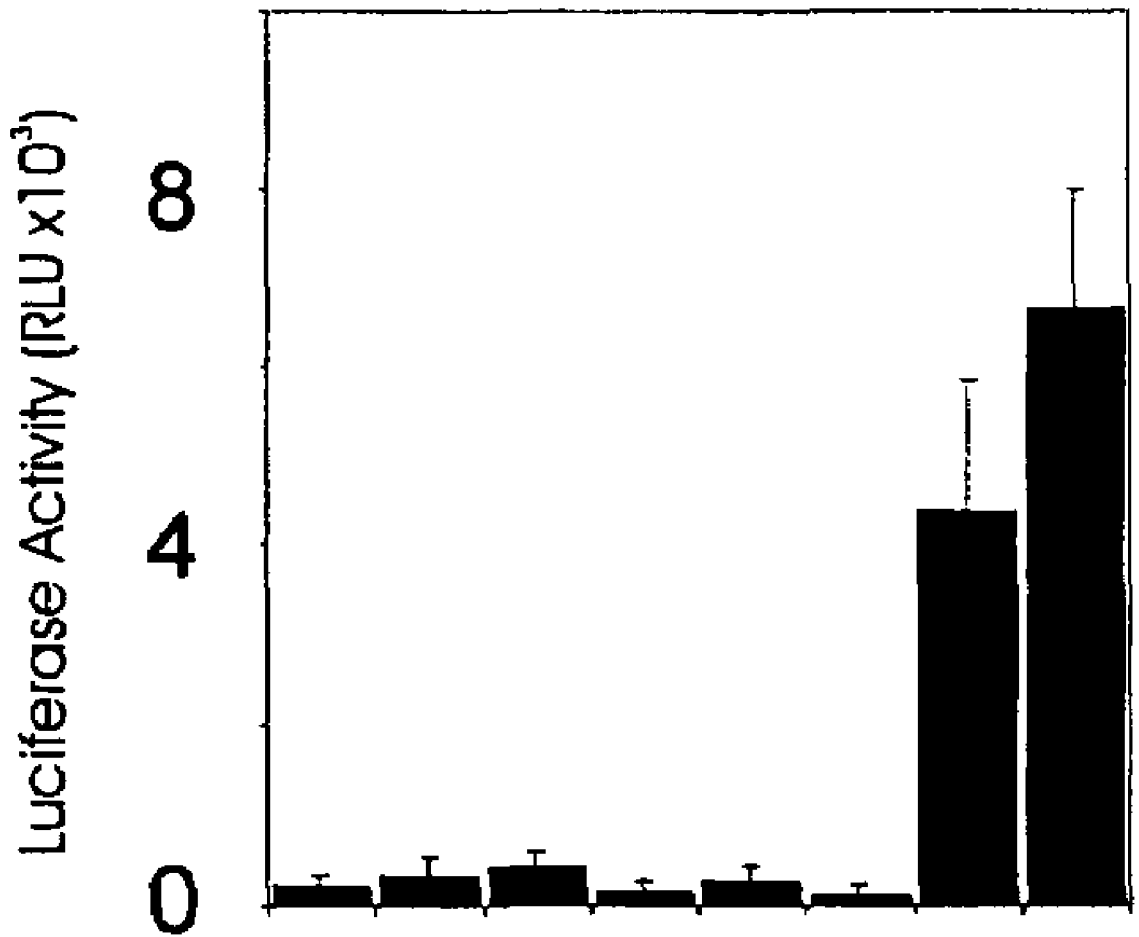
FIG. 11 shows that PRMT2 and PRMT3 also serve as coactivators for nuclear receptors. CV-1 cells were transiently transfected with expression vectors for the orphan (i.e. no ligand) nuclear receptor ERR3, and where indicated the expression vectors for GRIP1, CARM1, PRMT1, PRMT2, and PRMT3. Like PRMT1 (FIGS. 9 & 10), PRMT2 and PRMT3 could enhance nuclear receptor function in cooperation with CARM1.

Synergy of CARM1 with Histone Acetyl Transferases and other Protein Arginine Methyltransferases in Transcriptional Activation This example shows that CARM1 and other protein arginine methyltransferases synergistically activate transcription with each other and with histone acetyl transferases. As shown in FIGS. 9, 10 and 11, cells were transiently transfected with combinations of plasmids encoding GRIP1, CARM1, p300, PRMT1, PRMT2, and PRMT3. At low levels of expression of an appropriate nuclear receptor, in this case estrogen receptor (ER), a combination of GRIP1, CARM1 and p300 are required for activation of the ER-dependent receptor gene (FIG. 10B, left side). Similar effects are observed if PRMT1 is substituted for CARM1, other p160 coactivators are substituted for GRIP1, or CBP or P/CAF is substituted for p300. P300, CBP, and P/CAF all have histone acetyltransferase activity. This indicated that histone methyltransferases and histone acetyltransferases have cooperative or synergistic coactivator activity and suggests that methylation and acetylation of histones and/or other proteins in the transcription complex are cooperative processes in the activation of transcription.

The activity of CARM1 is also synergistic with those of PRMT1, PRMT2 or PRMT3. In cells expressing low levels of the orphan (i.e. no ligand) receptor, ERR1 or, ERR3, cotransfection of cells with plasmids encoding GRIP1, CARM1 and PRMT1 results in highly increased reporter gene expression as shown in FIG. 10A. The synergy between CARM1 and PRMT1 is also observed with three other nuclear receptors: estrogen, androgen, and thyroid hormone receptors (FIG. 9). FIG. 11 shows that CARM1 also acts synergistically with either PRMT2 or PRMT3.

Furthermore, due to the very high degree of dependence of the reporter gene activity on the presence of CARM1 and/or PRMT1, these conditions may prove useful for screening for inhibitors of the methyltransferase activity or the coactivator activity associated with these methyltransferases. Such transiently tranfected cells when they contain low levels of a nuclear receptor will express the nuclear receptor-dependent reporter gene, in this case luciferase, only in the presence of GRIP1, CARM1 and p300. Molecules that inhibit either the enzymatic activities of these coactivators or the protein-protein interactions of these coactivators would reduce the level of signal from the reporter gene.

EXAMPLE 10

Anti-CARM1 Antibody

The peptide SEQ ID NO: 6: (C)SPMSIPTNTMHYGS-COOH, representing the C-terminal CARM1 amino acid residues 595–608 was coupled to KLH and injected into rabbits. The (C) is not part of the CARM1 sequence but was added for coupling to KLH. The antiserum was tested at a dilution of 1:2000 in western blotting. The positive control was CARM1translated in vitro with no radioactive amino acids; the negative control was a parallel in vitro translation reaction with no CARM1 mRNA. Products from these two reactions were separated by molecular weight by SDS-polyacrylamide gel electrophoresis, and the proteins were transferred from the gel to a nylon membrane. The membrane was incubated with the CARM1 antiserm, a secondary HRP-coupled antibody, and visualized by luminescence. The positive control gave a very strong band at the expected size for CARM1, while the negative control gave no band at that position.

All of the publications which are cited within the body of the instant specification are hereby incorporated by reference in their entirety.

TABLE 2

SEQ ID NO: 1. *M. musculuc* cDNA for CARM1 (GenBank Accession No. AF117887).

| | | | | | |
|---|---|---|---|---|---|
| 1 | aggggggcctg | gagccggacc | taagatggca | gcggcggcag | cgacggcggt | ggggccgggt |
| 61 | gcggggagcg | ctggggtggc | gggcccgggc | ggcgcggggc | cctgcgctac | agtgtctgtg |
| 121 | ttcccgggcg | cccgcctcct | cactatcggc | gacgcgaacg | gcgagatcca | gcggcacgcg |
| 181 | gagcagcagg | cgctgcgcct | tgaggtgcgc | gccggaccag | acgcggcggg | catcgccctc |
| 241 | tacagccatg | aagatgtgtg | tgttttcaag | tgctcggtgt | cccgagagac | agagtgcagt |
| 301 | cgtgtgggca | gacagtcctt | catcatcacc | ctgggctgca | acagcgtcct | catccagttt |
| 361 | gccacacccc | acgatttctg | ttctttctac | aacatcctga | aaacctgtcg | ggccacaca |
| 421 | ctggagcgct | ctgtgttcag | tgagcggaca | gaggaatcct | cagctgtgca | gtacttccag |
| 481 | ttctatggct | acctatccca | gcagcagaac | atgatgcagg | actatgtgcg | gacaggcacc |
| 541 | taccagcgtg | cgatcctgca | gaaccacacg | gacttcaagg | acaagatcgt | tctagatgtg |

TABLE 2-continued

SEQ ID NO: 1. *M. musculuc* cDNA for CARM1 (GenBank Accession No. AF117887).

```
 601 ggctgtggct ctgggatcct gtcattttt gctgctcaag caggagccag gaaaatttat
 661 gcagtggaag ccagcaccat ggctcagcat gcagaggtcc tggtgaagag taacaatctg
 721 acagaccgca tcgtggtcat ccctggcaaa gtagaggagg tctcattgcc tgagcaagtg
 781 gacattatca tctcagagcc catgggctac atgctcttca atgaacgaat gctcgagagc
 841 tacctccatg ccaaaaagta cctgaagcct agtggaaaca tgttccccac cattggtgat
 901 gtccacctcg caccctttcac tgatgaacag ctctacatgg agcagttcac caaagccaac
 961 ttccggtacc agccatcctt ccatggagtg gacctgtcgg ccctcagagg tgccgctgtg
1021 gatgagtact tccggcaacc tgtggtggac acatttgaca tccggatcct gatggccaaa
1081 tctgtcaagt acacagtgaa cttcttagaa gccaagaag gcgatttgca caggatagaa
1141 atcccattca aattccacat gctgcattca gggctagtcc atggcttggc cttctggttC
1201 gatgttgctt tcattggctc cataatgacc gtgtggctat ccacagcccc aacagagccc
1261 ctgacccact ggtaccaggt ccggtgcctc ttccagtcac cgttgtttgc caaggccggg
1321 gacacgctct cagggacatg tctgcttatt gccaacaaaa gacagagcta tgacatcagt
1381 attgtggcac aggtggacca gacaggctcc aagtccagta acctgctgga tctaaagaac
1441 cccttcttca ggtacacagg tacaaccca tcaccccac ctggctcaca ctacacgtct
1501 ccctcggaga atatgtggaa cacaggaagc acctataatc tcagcagcgg ggtggctgtg
1561 gctggaatgc ctactgccta cgacctgagc agtgttattg ccggcggctc cagtgtgggt
1621 cacaacaacc tgattccctt agctaacaca gggattgtca atcacaccca ctcccggatg
1681 ggctccataa tgagcacggg cattgtccaa ggctcctcag gtgcccaggg aggcggcggt
1741 agctccagtg cccactatgc agtcaacaac cagttcacca tgggtggccc tgccatctct
1801 atggcctcgc ccatgtccat cccgaccaac accatgcact atgggagtta ggtgcctcca
1861 gccgcgacag cactgcgcac tgacagcacc aggaaaccaa atcaagtcca ggcccggcac
1921 agccagtggc tgttccccct tgttctggag aagttgttga acacccggtc acagcctcct
1981 tgctatggga acttggacaa ttttgtacac gatgtcgccg ctgcccctcaa gtaccccag
2041 cccaaccttt ggtcccgagc gcgtgttgct gccatacttt acatgagatc ctgttgggc
2101 agccctcatc ctgttctgta ctctccactc tgacctggct ttgacatctg ctggaagagg
2161 caagtcctcc cccaaccccc acagctgcac ctgaccaggc aggaggaggc cagcagctgc
2221 caccacagac ctggcagcac ccaccccaca acccgtcctt gcacctcccc tcacctgggg
2281 tggcagcaca gccagctgga cctctccttc aactaccagg ccacatggtc accatgggcg
2341 tgacatgctc ctttttttaa ttttattttt ttacgaaaag aaccagtgtc aacccacaga
2401 ccctctgaga aacccggctg gcgcgccaag ccagcagccc ctgttcctag gcccagaggt
2461 tctaggtgag gggtggccct gtcaagcctt cagagtgggc acagcccctc ccaccaaagg
2521 gttcacctca aacttgaatg tacaaaccac ccagctgtcc aaaggcctag tccctacttt
2581 ctgctactgt cctgtcctga gccctgaagg ccccctcca tcaaaagctt gaacaggcag
2641 cccagagtgt gtcaccctgg gctactgggg cagacaagaa acctcaaaga tctgtcacac
2701 acacacaagg aaggcgtcct ctcctgatag ctgacatagg cctgtgtgtt gcgttcacat
```

TABLE 2-continued

SEQ ID NO: 1. *M. musculuc* cDNA for CARM1 (GenBank Accession No. AF117887).

```
2761 tcatgttcta cttaatcctc tcaagacagc aaccctggga aggagcctcg cagggacctc 2821 cccagacaag aagaaaagca aacaaggaag ggtgattaat aagcacaggc agtttcccct 2881 attcccttac cctagagtcc ccacctgaat ggccacagcc tgccacagga accccttggc 2941 aaaggctgga gctgctctgt gccaccctcc tgacctgtca gggaatcaca gggccctcag 3001 gcagctggga accaggctct ctcctgtcca tcagtaatac tccttgctcg gatggccctc 3061 ccccaccttt atataaattc tctggatcac ctttgcatag aaaataaaag tgtttgcttt 3121 gtaa
```

TABLE 3

SEQ ID NO: 2. Deduced amino acid sequence of CARM1 (GenBank Accession No. AAD41265).

```
  1 maaaaatavg pgagsagvag pggagpcatv svfpgarllt igdangeiqr haeqqalrle 61 vragpdaagi alyshedvcv fkcsvsrete csrvgrqsfi itlgcnsvli qfatphdfcs 121 fynilktcrg htlersvfse rteessavqy fqfygylsqq qnmmqdyvrt gtyqrailqn 181 htdfkdkivl dvgcgsgils ffaaqagark iyaveastma qhaevlvksn nltdrivvip 241 gkveevslpe qvdiiisepm gymlfnerml esylhakkyl kpsgnmfpti gdvhlapftd 301 eqlymeqftk anfryqpsfh gvdlsalrga avdeyfrqpv vdtfdirilm aksvkytvnf 361 leakegdlhr ieipfkfhml hsglvhglaf wfdvafigsi mtvwlstapt eplthwyqvr 421 clfqsplfak agdtlsgtcl liankrqsyd isivaqvdqt gskssnlldl knpffrytgt 481 tpspppgshy tspsenmwnt gstynlssgv avagmptayd lssviaggss vghnnlipla 541 ntgivnhths rmgsimstgi vqgssgaqgg ggsssahyav nnqftmggpa ismaspmsip 601 tntmhygs
```

TABLE 4

SEQ ID NO: 3. Sequence of CARM1 VLD to AAA variant.

```
  1 maaaaatavg pgagsagvag pggagpcatv svfpgarllt igdangeiqr haeqqalrle 61 vragpdaagi alyshedvcv fkcsvsrete csrvgrqsfi itlgcnsvli qfatphdfcs 121 fynilktcrg htlersvfse rteessavqy fqfygylsqq qnmmqdyvrt gtyqrailqn 181 htdfkdkiaa avgcgsgils ffaaqagark iyaveastma qhaevlvksn nltdrivvip 241 gkveevslpe qvdiiisepm gymlfnerml esylhakkyl kpsgnmfpti gdvhlapftd 301 eqlymeqftk anfryqpsfh gvdlsalrga avdeyfrqpv vdtfdirilm aksvkytvnf 361 leakegdlhr ieipfkfhml hsglvhglaf wfdvafigsi mtvwlstapt eplthwyqvr 421 clfqsplfak agdtlsgtcl liankrqsyd isivaqvdqt gskssnlldl knpffrytgt 481 tpspppgshy tspsenmwnt gstynlssgv avagmptayd lssviaggss vghnnlipla 541 ntgivnhths rmgsimstgi vqgssgaqgg ggsssahyav nnqftmggpa ismaspmsip 601 tntmhygs
```

TABLE 5

| SEQ ID NOS: 4 and 5. Peptides used for in vitro methylation experiments. | | |
|---|---|---|
| R1 peptide | SEQ ID NO: 4 | GGFGGRGGFG |
| K1 peptide | SEQ ID NO: 5 | GGFGGKGGFG |

TABLE 6

| SEQ ID NO: 6. Peptide used to generate anti-CARM1 antisera. | |
|---|---|
| SEQ ID NO: 6: | CSPMSIPTNTMHYGS |

TABLE 7

SEQ ID NO: 7. Human PRMT1 (GenBank Accession No. CAA71765).

```
  1 mevscgqaes sekpnaedmt skdyyfdsya hfgiheemlk devrtltyrn smfhnrhlfk
 61 dkvvldvgsg tgilcmfaak agarkvigiv cssisdyavk ivkankldhv vtiikgkvee
121 velpvekvdi iisewmgycl fyesmlntvl yardkwlapd glifpdratl yvtaiedrqy
181 kdykihwwen vygfdmscik dvaikeplvd vvdpkqlvtn aclikevdiy tvkvedltft
241 spfclqvkrn dyvhalvayf nieftrchkr tgfstspesp ythwkqtvfy medyltvktg
301 eeifgtigmr pnaknnrdld ftidldfkgq lcelscstdy rmr
```

TABLE 8

SEQ ID NO: 8. Human PRMT2 (GenBank Accession No. CAA67599)

```
  1 matsgdcprs esqgeepaec seagllqegv qpeefvaiad yaatdetqls flrgekilil
 61 rqttadwwwg eragccgyip anhvgkhvde ydpedtwqde eyfgsygtlk lhlemladqp
121 rttkyhsvil qnkesltdkv ildvgcgtgi islfcahyar pravyaveas emaqhtgqlv
181 lqngfadiit vyqqkvedvv lpekvdvlvs ewmgtcllfe fmiesilyar dawlkedgvi
241 wptmaalhlv pcsadkdyrs kvlfwdnaye fnlsalksla vkeffskpky nhilkpedcl
301 sepctilqld mrtvqisdle tlrgelrfdi rkagtlhgft awfsvhfqsl qegqppqvls
361 tgpfhptthw kqtlfmmddp vphtgdvvt gsvvlqrnpv wrrhmsvals wavtsrqdpt
421 sqkvgekvfp iwr
```

TABLE 9

SEQ ID NO: 9. Human PRMT3 (GenBank Accession No. AAC39837)

```
  1 depelsdsgd eaawededda dlphgkqqtp clfcnrlfts aeetfshcks ehqfnidsmv
 61 hkhglefygy iklinfirlk nptveymnsi ynpvpwekee ylkpvleddl llqfdvedly
121 epvsvpfsyp nglsentsvv eklkhmeara lsaeaalara redlqkmkqf aqdfvmhtdv
181 rtcssstsvi adlqededgv yfssyghygi heemlkdkir tesyrdfiyq nphifkdkvv
241 ldvgcgtgil smfaakagak kvlgvdqsei lyqamdiirl nkledtitli kgkieevhlp
301 vekvdviise wmgyfllfes mldsvlyakn kylakggsvy pdictislva vsdvnkhadr
361 iafwddvygf kmscmkkavi peavvevldp ktlisepcgi khidchttsi sdlefssdft
421 lkitrtsmct aiagyfdiyf eknchnrvvf stgpqstkth wkqtvfllek pfsvkageal
481 kgkvtvhknk kdprsltvtl tlnnstqtyg lg
```

TABLE 10

SEQ ID NO: 10. Yease ODP1 Protein Arginine Methyltransferase.
(GenBank Accession No. 6319508)

```
  1 msktavkdsa tektklsese qhyfnsydhy giheemlqdt vrtlsyrnai iqnkdlfkdk
 61 ivldvgcgtg ilsmfaakhg akhvigvdms siiemakelv elngfsdkit llrgkledvh
121 lpfpkvdiii sewmgyflly esmmdtvlya rdhylveggl ifpdkcsihl agledsqykd
181 eklnywqdvy gfdyspfvpl vlhepivdtv ernnvnttad kliefdlntv kisdlafksn
241 fkltakrqdm ingivtwfdi vfpapkgkrp vefstgphap ythwkqtify fpddldaetg
301 dtiegelvcs pneknnrdln ikisykfesn gidgnsrsrk negsylmh
```

The invention claimed is:

1. A method for methylating arginine amino acid residues within a histone polypeptide comprising contacting a polypeptide encoded by an isolated nucleic acid molecule comprising SEQ ID NO:1 or a complementary sequence thereof, or a polypeptide comprising SEQ ID NO:2, with said histone polypeptide in the presence of S-adenosylmethionine.

2. A method of claim 1, wherein said histone is histone H3.

* * * * *

UNITED STATES PATENT AND TRADEMARK OFFICE
CERTIFICATE OF CORRECTION

| | |
|---|---|
| PATENT NO. | : 7,214,510 B2 |
| APPLICATION NO. | : 10/830591 |
| DATED | : May 8, 2007 |
| INVENTOR(S) | : Michael R. Stallcup et al. |

It is certified that error appears in the above-identified patent and that said Letters Patent is hereby corrected as shown below:

Column 1, lines 15-17, which currently reads "The government may have certain rights in this invention pursuant to grants DK43093 and NS17269 from the National Institutes of Health", should be replaced with -- This invention was made with government support under Contract Nos. R01 DK043093 and NS017269 awarded by the National Institutes of Health. The government has certain rights in the invention. --

Signed and Sealed this

Tenth Day of November, 2009

David J. Kappos
*Director of the United States Patent and Trademark Office*

SEQUENCE LISTING

<160> NUMBER OF SEQ ID NOS: 10

<210> SEQ ID NO 1
<211> LENGTH: 3124
<212> TYPE: DNA
<213> ORGANISM: Mus musculuc

<400> SEQUENCE: 1

```
aggggggcctg gagccggacc taagatggca gcggcggcag cgacggcggt ggggccgggt      60
gcggggagcg ctggggtggc gggcccgggc ggcgcgggggc cctgcgctac agtgtctgtg     120
ttcccgggcg cccgcctcct cactatcggc gacgcgaacg gcgagatcca gcggcacgcg     180
gagcagcagg cgctgcgcct tgaggtgcgc gccggaccag acgcggcggg catcgccctc     240
tacagccatg aagatgtgtg tgttttcaag tgctcggtgt cccgagagac agagtgcagt     300
cgtgtgggca gacagtcctt catcatcacc ctgggctgca acagcgtcct catccagttt     360
gccacacccc acgatttctg ttctttctac aacatcctga aaacctgtcg gggccacaca     420
ctggagcgct ctgtgttcag tgagcggaca gaggaatcct cagctgtgca gtacttccag     480
ttctatggct acctatccca gcagcagaac atgatgcagg actatgtgcg acaggcacc     540
taccagcgtg cgatcctgca gaaccacacg gacttcaagg acaagatcgt tctagatgtg     600
ggctgtggct ctgggatcct gtcatttttt gctgctcaag caggagccag gaaaatttat     660
gcagtggaag ccagcaccat ggctcagcat gcagaggtcc tggtgaagag taacaatctg     720
acagaccgca tcgtggtcat ccctggcaaa gtagaggagg tctcattgcc tgagcaagtg     780
gacattatca tctcagagcc catgggctac atgctcttca atgaacgaat gctcgagagc     840
tacctccatg ccaaaaagta cctgaagcct agtggaaaca tgttcccccac cattggtgat     900
gtccacctcg caccttcac tgatgaacag ctctacatgg agcagttcac caaagccaac     960
ttccggtacc agccatcctt ccatggagtg gacctgtcgg ccctcagagg tgccgctgtg    1020
gatgagtact tccggcaacc tgtggtggac acatttgaca tccggatcct gatggccaaa    1080
tctgtcaagt acacagtgaa cttcttagaa gccaaagaag gcgatttgca caggatagaa    1140
atcccattca aattccacat gctgcattca gggctagtcc atggcttggc cttctggttc    1200
gatgttgctt tcattggctc cataatgacc gtgtggctat ccacagccccc aacagagccc    1260
ctgacccact ggtaccaggt ccggtgcctc ttccagtcac cgttgtttgc caaggccggg    1320
gacacgctct caggacatg tctgcttatt gccaacaaaa gacagagcta tgacatcagt    1380
attgtggcac aggtggacca gacaggctcc aagtccagta acctgctgga tctaaagaac    1440
```

-continued

```
cccttcttca ggtacacagg tacaacccca tcaccccac ctggctcaca ctacacgtct   1500
ccctcggaga atatgtggaa cacaggaagc acctataatc tcagcagcgg ggtggctgtg   1560
gctggaatgc ctactgccta cgacctgagc agtgttattg ccggcggctc cagtgtgggt   1620
cacaacaacc tgattccctt agctaacaca gggattgtca atcacaccca ctcccggatg   1680
ggctccataa tgagcacggg cattgtccaa ggctcctcag gtgcccaggg aggcggcggt   1740
agctccagtg cccactatgc agtcaacaac cagttcacca tgggtggccc tgccatctct   1800
atggcctcgc ccatgtccat cccgaccaac accatgcact atgggagtta ggtgcctcca   1860
gccgcgacag cactgcgcac tgacagcacc aggaaaccaa atcaagtcca ggcccggcac   1920
agccagtggc tgttccccct tgttctggag aagttgttga cacccggtc acagcctcct   1980 tgctatggga acttggacaa ttttgtacac gatgtcgccg ctgccctcaa gtaccccag   2040 cccaaccttt ggtcccgagc gcgtgttgct gccatacttt acatgagatc ctgttggggc   2100
agccctcatc ctgttctgta ctctccactc tgacctggct ttgacatctg ctggaagagg   2160
caagtcctcc cccaacccc acagctgcac ctgaccaggc aggaggaggc cagcagctgc   2220
caccacagac ctggcagcac ccaccccaca acccgtcctt gcacctcccc tcacctgggg   2280
tggcagcaca gccagctgga cctctccttc aactaccagg ccacatggtc ccatgggcg   2340 tgacatgctg cttttttaa tttattttt ttacgaaaag aaccagtgtc aacccacaga   2400
ccctctgaga aacccggctg gcgcgccaag ccagcagccc ctgttcctag gcccagaggt   2460
tctaggtgag gggtggccct gtcaagcctt cagagtgggc acagcccctc ccaccaaagg   2520
gttcacctca aacttgaatg tacaaaccac ccagctgtcc aaaggcctag tccctacttt   2580
ctgctactgt cctgtcctga gccctgaagg ccccctcca tcaaagctt gaacaggcag   2640 cccagagtgt gtcaccctgg gctactgggg cagacaagaa acctcaaaga tctgtcacac   2700
acacacaagg aaggcgtcct ctcctgatag ctgacatagg cctgtgtgtt gcgttcacat   2760
tcatgttcta cttaatcctc tcaagacagc aaccctggga aggagcctcg cagggacctc   2820
cccagacaag aagaaaagca aacaaggaag ggtgattaat aagcacaggc agtttcccct   2880
attcccttac cctagagtcc ccacctgaat ggccacagcc tgccacagga accccttggc   2940
aaaggctgga gctgctctgt gccacccctcc tgacctgtca gggaatcaca gggccctcag   3000
gcagctggga accaggctct ctcctgtcca tcagtaatac tccttgctcg gatggccctc   3060
ccccaccttt atataaattc tctggatcac ctttgcatag aaaataaaag tgtttgcttt   3120
gtaa                                                                3124
```

<210> SEQ ID NO 2
<211> LENGTH: 608
<212> TYPE: PRT
<213> ORGANISM: Artificial Sequence
<220> FEATURE:
<223> OTHER INFORMATION: Deduced amino acid sequence of CARM1

<400> SEQUENCE: 2

```
Met Ala Ala Ala Ala Ala Thr Ala Val Gly Pro Gly Ala Gly Ser Ala
 1               5                  10                  15

Gly Val Ala Gly Pro Gly Gly Ala Gly Pro Cys Ala Thr Val Ser Val
            20                  25                  30

Phe Pro Gly Ala Arg Leu Leu Thr Ile Gly Asp Ala Asn Gly Glu Ile
        35                  40                  45

Gln Arg His Ala Glu Gln Gln Ala Leu Arg Leu Glu Val Arg Ala Gly
```

```
               50                  55                  60
Pro Asp Ala Ala Gly Ile Ala Leu Tyr Ser His Glu Asp Val Cys Val
 65                  70                  75                  80

Phe Lys Cys Ser Val Ser Arg Glu Thr Glu Cys Ser Arg Val Gly Arg
                 85                  90                  95

Gln Ser Phe Ile Ile Thr Leu Gly Cys Asn Ser Val Leu Ile Gln Phe
                100                 105                 110

Ala Thr Pro His Asp Phe Cys Ser Phe Tyr Asn Ile Leu Lys Thr Cys
                115                 120                 125

Arg Gly His Thr Leu Glu Arg Ser Val Phe Ser Glu Arg Thr Glu Glu
            130                 135                 140

Ser Ser Ala Val Gln Tyr Phe Gln Phe Gly Tyr Leu Ser Gln Gln
145                 150                 155                 160

Gln Asn Met Met Gln Asp Tyr Val Arg Thr Gly Thr Tyr Gln Arg Ala
                165                 170                 175

Ile Leu Gln Asn His Thr Asp Phe Lys Asp Lys Ile Val Leu Asp Val
                180                 185                 190

Gly Cys Gly Ser Gly Ile Leu Ser Phe Phe Ala Gln Ala Gly Ala
        195                 200                 205

Arg Lys Ile Tyr Ala Val Glu Ala Ser Thr Met Ala Gln His Ala Glu
        210                 215                 220

Val Leu Val Lys Ser Asn Asn Leu Thr Asp Arg Ile Val Ile Pro
225                 230                 235                 240

Gly Lys Val Glu Glu Val Ser Leu Pro Glu Gln Val Asp Ile Ile Ile
                245                 250                 255

Ser Glu Pro Met Gly Tyr Met Leu Phe Asn Glu Arg Met Leu Glu Ser
                260                 265                 270

Tyr Leu His Ala Lys Lys Tyr Leu Lys Pro Ser Gly Asn Met Phe Pro
            275                 280                 285

Thr Ile Gly Asp Val His Leu Ala Pro Phe Thr Asp Glu Gln Leu Tyr
        290                 295                 300

Met Glu Gln Phe Thr Lys Ala Asn Phe Arg Tyr Gln Pro Ser Phe His
305                 310                 315                 320

Gly Val Asp Leu Ser Ala Leu Arg Gly Ala Ala Val Asp Glu Tyr Phe
                325                 330                 335

Arg Gln Pro Val Val Asp Thr Phe Asp Ile Arg Ile Leu Met Ala Lys
                340                 345                 350

Ser Val Lys Tyr Thr Val Asn Phe Leu Glu Ala Lys Glu Gly Asp Leu
            355                 360                 365

His Arg Ile Glu Ile Pro Phe Lys Phe His Met Leu His Ser Gly Leu
    370                 375                 380

Val His Gly Leu Ala Phe Trp Phe Asp Val Ala Phe Ile Gly Ser Ile
385                 390                 395                 400

Met Thr Val Trp Leu Ser Thr Ala Pro Thr Glu Pro Leu Thr His Trp
                405                 410                 415

Tyr Gln Val Arg Cys Leu Phe Gln Ser Pro Leu Phe Ala Lys Ala Gly
            420                 425                 430

Asp Thr Leu Ser Gly Thr Cys Leu Leu Ile Ala Asn Lys Arg Gln Ser
            435                 440                 445

Tyr Asp Ile Ser Ile Val Ala Gln Val Asp Gln Thr Gly Ser Lys Ser
        450                 455                 460

Ser Asn Leu Leu Asp Leu Lys Asn Pro Phe Phe Arg Tyr Thr Gly Thr
465                 470                 475                 480
```

-continued

```
Thr Pro Ser Pro Pro Gly Ser His Tyr Thr Ser Pro Ser Glu Asn
            485                 490                 495
Met Trp Asn Thr Gly Ser Thr Tyr Asn Leu Ser Ser Gly Val Ala Val
            500                 505                 510
Ala Gly Met Pro Thr Ala Tyr Asp Leu Ser Ser Val Ile Ala Gly Gly
            515                 520                 525
Ser Ser Val Gly His Asn Asn Leu Ile Pro Leu Ala Asn Thr Gly Ile
            530                 535                 540
Val Asn His Thr His Ser Arg Met Gly Ser Ile Met Ser Thr Gly Ile
545                 550                 555                 560
Val Gln Gly Ser Ser Gly Ala Gln Gly Gly Gly Ser Ser Ser Ala
            565                 570                 575
His Tyr Ala Val Asn Asn Gln Phe Thr Met Gly Gly Pro Ala Ile Ser
            580                 585                 590
Met Ala Ser Pro Met Ser Ile Pro Thr Asn Thr Met His Tyr Gly Ser
            595                 600                 605
```

<210> SEQ ID NO 3
<211> LENGTH: 608
<212> TYPE: PRT
<213> ORGANISM: Artificial Sequence
<220> FEATURE:
<223> OTHER INFORMATION: CARM1 VLD TO AAA Variant

<400> SEQUENCE: 3

```
Met Ala Ala Ala Ala Thr Ala Val Gly Pro Gly Ala Gly Ser Ala
1               5                   10                  15
Gly Val Ala Gly Pro Gly Gly Ala Gly Pro Cys Ala Thr Val Ser Val
            20                  25                  30
Phe Pro Gly Ala Arg Leu Leu Thr Ile Gly Asp Ala Asn Gly Glu Ile
            35                  40                  45
Gln Arg His Ala Glu Gln Gln Ala Leu Arg Leu Glu Val Arg Ala Gly
            50                  55                  60
Pro Asp Ala Ala Gly Ile Ala Leu Tyr Ser His Glu Asp Val Cys Val
65                  70                  75                  80
Phe Lys Cys Ser Val Ser Arg Glu Thr Glu Cys Ser Arg Val Gly Arg
            85                  90                  95
Gln Ser Phe Ile Ile Thr Leu Gly Cys Asn Ser Val Leu Ile Gln Phe
            100                 105                 110
Ala Thr Pro His Asp Phe Cys Ser Phe Tyr Asn Ile Leu Lys Thr Cys
            115                 120                 125
Arg Gly His Thr Leu Glu Arg Ser Val Phe Ser Glu Arg Thr Glu Glu
            130                 135                 140
Ser Ser Ala Val Gln Tyr Phe Gln Phe Tyr Gly Tyr Leu Ser Gln Gln
145                 150                 155                 160
Gln Asn Met Met Gln Asp Tyr Val Arg Thr Gly Thr Tyr Gln Arg Ala
            165                 170                 175
Ile Leu Gln Asn His Thr Asp Phe Lys Asp Lys Ile Ala Ala Ala Val
            180                 185                 190
Gly Cys Gly Ser Gly Ile Leu Ser Phe Phe Ala Ala Gln Ala Gly Ala
            195                 200                 205
Arg Lys Ile Tyr Ala Val Glu Ala Ser Thr Met Ala Gln His Ala Glu
            210                 215                 220
Val Leu Val Lys Ser Asn Asn Leu Thr Asp Arg Ile Val Val Ile Pro
225                 230                 235                 240
```

Gly Lys Val Glu Glu Val Ser Leu Pro Glu Gln Val Asp Ile Ile Ile
                245                 250                 255

Ser Glu Pro Met Gly Tyr Met Leu Phe Asn Glu Arg Met Leu Glu Ser
            260                 265                 270

Tyr Leu His Ala Lys Lys Tyr Leu Lys Pro Ser Gly Asn Met Phe Pro
        275                 280                 285

Thr Ile Gly Asp Val His Leu Ala Pro Phe Thr Asp Glu Gln Leu Tyr
    290                 295                 300

Met Glu Gln Phe Thr Lys Ala Asn Phe Arg Tyr Gln Pro Ser Phe His
305                 310                 315                 320

Gly Val Asp Leu Ser Ala Leu Arg Gly Ala Ala Val Asp Glu Tyr Phe
                325                 330                 335

Arg Gln Pro Val Val Asp Thr Phe Asp Ile Arg Ile Leu Met Ala Lys
            340                 345                 350

Ser Val Lys Tyr Thr Val Asn Phe Leu Glu Ala Lys Glu Gly Asp Leu
        355                 360                 365

His Arg Ile Glu Ile Pro Phe Lys Phe His Met Leu His Ser Gly Leu
    370                 375                 380

Val His Gly Leu Ala Phe Trp Phe Asp Val Ala Phe Ile Gly Ser Ile
385                 390                 395                 400

Met Thr Val Trp Leu Ser Thr Ala Pro Thr Glu Pro Leu Thr His Trp
                405                 410                 415

Tyr Gln Val Arg Cys Leu Phe Gln Ser Pro Leu Phe Ala Lys Ala Gly
            420                 425                 430

Asp Thr Leu Ser Gly Thr Cys Leu Leu Ile Ala Asn Lys Arg Gln Ser
        435                 440                 445

Tyr Asp Ile Ser Ile Val Ala Gln Val Asp Gln Thr Gly Ser Lys Ser
    450                 455                 460

Ser Asn Leu Leu Asp Leu Lys Asn Pro Phe Phe Arg Tyr Thr Gly Thr
465                 470                 475                 480

Thr Pro Ser Pro Pro Pro Gly Ser His Tyr Thr Ser Pro Ser Glu Asn
                485                 490                 495

Met Trp Asn Thr Gly Ser Thr Tyr Asn Leu Ser Ser Gly Val Ala Val
            500                 505                 510

Ala Gly Met Pro Thr Ala Tyr Asp Leu Ser Ser Val Ile Ala Gly Gly
        515                 520                 525

Ser Ser Val Gly His Asn Asn Leu Ile Pro Leu Ala Asn Thr Gly Ile
    530                 535                 540

Val Asn His Thr His Ser Arg Met Gly Ser Ile Met Ser Thr Gly Ile
545                 550                 555                 560

Val Gln Gly Ser Ser Gly Ala Gln Gly Gly Gly Ser Ser Ser Ala
                565                 570                 575

His Tyr Ala Val Asn Asn Gln Phe Thr Met Gly Gly Pro Ala Ile Ser
            580                 585                 590

Met Ala Ser Pro Met Ser Ile Pro Thr Asn Thr Met His Tyr Gly Ser
        595                 600                 605

<210> SEQ ID NO 4
<211> LENGTH: 10
<212> TYPE: PRT
<213> ORGANISM: Artifical Sequence
<220> FEATURE:
<223> OTHER INFORMATION: Peptide used for in vitro methylation
      experiments -continued

```
<400> SEQUENCE: 4

Gly Gly Phe Gly Gly Arg Gly Gly Phe Gly
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Peptide used for in vitro methylation
      experiments

<400> SEQUENCE: 5

Gly Gly Phe Gly Gly Lys Gly Gly Phe Gly
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Peptide used to generate anti-CARM1 antisera

<400> SEQUENCE: 6

Cys Ser Pro Met Ser Ile Pro Thr Asn Thr Met His Tyr Gly Ser
1               5                   10                  15

<210> SEQ ID NO 7
<211> LENGTH: 343
<212> TYPE: PRT
<213> ORGANISM: Artifical Sequence
<220> FEATURE:
<223> OTHER INFORMATION: Human PRMT1

<400> SEQUENCE: 7

Met Glu Val Ser Cys Gly Gln Ala Glu Ser Ser Glu Lys Pro Asn Ala
1               5                   10                  15

Glu Asp Met Thr Ser Lys Asp Tyr Tyr Phe Asp Ser Tyr Ala His Phe
                20                  25                  30

Gly Ile His Glu Glu Met Leu Lys Asp Glu Val Arg Thr Leu Thr Tyr
            35                  40                  45

Arg Asn Ser Met Phe His Asn Arg His Leu Phe Lys Asp Lys Val Val
    50                  55                  60

Leu Asp Val Gly Ser Gly Thr Gly Ile Leu Cys Met Phe Ala Ala Lys
65                  70                  75                  80

Ala Gly Ala Arg Lys Val Ile Gly Ile Val Cys Ser Ile Ser Asp
                85                  90                  95

Tyr Ala Val Lys Ile Val Lys Ala Asn Lys Leu Asp His Val Val Thr
                100                 105                 110

Ile Ile Lys Gly Lys Val Glu Glu Val Glu Leu Pro Val Glu Lys Val
            115                 120                 125

Asp Ile Ile Ile Ser Glu Trp Met Gly Tyr Cys Leu Phe Tyr Glu Ser
    130                 135                 140

Met Leu Asn Thr Val Leu Tyr Ala Arg Asp Lys Trp Leu Ala Pro Asp
145                 150                 155                 160

Gly Leu Ile Phe Pro Asp Arg Ala Thr Leu Tyr Val Thr Ala Ile Glu
                165                 170                 175

Asp Arg Gln Tyr Lys Asp Tyr Lys Ile His Trp Trp Glu Asn Val Tyr
                180                 185                 190

Gly Phe Asp Met Ser Cys Ile Lys Asp Val Ala Ile Lys Glu Pro Leu
```

-continued

```
                195                 200                 205
Val Asp Val Asp Pro Lys Gln Leu Val Thr Asn Ala Cys Leu Ile
    210                 215                 220
Lys Glu Val Asp Ile Tyr Thr Val Lys Val Glu Asp Leu Thr Phe Thr
225                 230                 235                 240
Ser Pro Phe Cys Leu Gln Val Lys Arg Asn Asp Tyr Val His Ala Leu
                245                 250                 255
Val Ala Tyr Phe Asn Ile Glu Phe Thr Arg Cys His Lys Arg Thr Gly
                260                 265                 270
Phe Ser Thr Ser Pro Glu Ser Pro Tyr Thr His Trp Lys Gln Thr Val
            275                 280                 285
Phe Tyr Met Glu Asp Tyr Leu Thr Val Lys Thr Gly Glu Glu Ile Phe
            290                 295                 300
Gly Thr Ile Gly Met Arg Pro Asn Ala Lys Asn Asn Arg Asp Leu Asp
305                 310                 315                 320
Phe Thr Ile Asp Leu Asp Phe Lys Gly Gln Leu Cys Glu Leu Ser Cys
                325                 330                 335
Ser Thr Asp Tyr Arg Met Arg
            340
```

<210> SEQ ID NO 8
<211> LENGTH: 433
<212> TYPE: PRT
<213> ORGANISM: Artificial Sequence
<220> FEATURE:
<223> OTHER INFORMATION: Human PRMT2

<400> SEQUENCE: 8

```
Met Ala Thr Ser Gly Asp Cys Pro Arg Ser Glu Ser Gln Gly Glu Glu
1               5                   10                  15
Pro Ala Glu Cys Ser Glu Ala Gly Leu Leu Gln Glu Gly Val Gln Pro
                20                  25                  30
Glu Glu Phe Val Ala Ile Ala Asp Tyr Ala Ala Thr Asp Glu Thr Gln
            35                  40                  45
Leu Ser Phe Leu Arg Gly Glu Lys Ile Leu Ile Leu Arg Gln Thr Thr
50                  55                  60
Ala Asp Trp Trp Trp Gly Glu Arg Ala Gly Cys Cys Gly Tyr Ile Pro
65                  70                  75                  80
Ala Asn His Val Gly Lys His Val Asp Glu Tyr Asp Pro Glu Asp Thr
                85                  90                  95
Trp Gln Asp Glu Glu Tyr Phe Gly Ser Tyr Gly Thr Leu Lys Leu His
            100                 105                 110
Leu Glu Met Leu Ala Asp Gln Pro Arg Thr Thr Lys Tyr His Ser Val
            115                 120                 125
Ile Leu Gln Asn Lys Glu Ser Leu Thr Asp Lys Val Ile Leu Asp Val
130                 135                 140
Gly Cys Gly Thr Gly Ile Ile Ser Leu Phe Cys Ala His Tyr Ala Arg
145                 150                 155                 160
Pro Arg Ala Val Tyr Ala Val Glu Ala Ser Glu Met Ala Gln His Thr
                165                 170                 175
Gly Gln Leu Val Leu Gln Asn Gly Phe Ala Asp Ile Ile Thr Val Tyr
            180                 185                 190
Gln Gln Lys Val Glu Asp Val Val Leu Pro Glu Lys Val Asp Val Leu
            195                 200                 205
Val Ser Glu Trp Met Gly Thr Cys Leu Leu Phe Glu Phe Met Ile Glu
```

-continued

```
                 210                 215                 220
Ser Ile Leu Tyr Ala Arg Asp Ala Trp Leu Lys Glu Asp Gly Val Ile
225                 230                 235                 240

Trp Pro Thr Met Ala Ala Leu His Leu Val Pro Cys Ser Ala Asp Lys
                245                 250                 255

Asp Tyr Arg Ser Lys Val Leu Phe Trp Asp Asn Ala Tyr Glu Phe Asn
                260                 265                 270

Leu Ser Ala Leu Lys Ser Leu Ala Val Lys Glu Phe Phe Ser Lys Pro
            275                 280                 285

Lys Tyr Asn His Ile Leu Lys Pro Glu Asp Cys Leu Ser Glu Pro Cys
        290                 295                 300

Thr Ile Leu Gln Leu Asp Met Arg Thr Val Gln Ile Ser Asp Leu Glu
305                 310                 315                 320

Thr Leu Arg Gly Glu Leu Arg Phe Asp Ile Arg Lys Ala Gly Thr Leu
                325                 330                 335

His Gly Phe Thr Ala Trp Phe Ser Val His Phe Gln Ser Leu Gln Glu
                340                 345                 350

Gly Gln Pro Pro Gln Val Leu Ser Thr Gly Pro Phe His Pro Thr Thr
            355                 360                 365

His Trp Lys Gln Thr Leu Phe Met Met Asp Asp Pro Val Pro Val His
        370                 375                 380

Thr Gly Asp Val Val Thr Gly Ser Val Val Leu Gln Arg Asn Pro Val
385                 390                 395                 400

Trp Arg Arg His Met Ser Val Ala Leu Ser Trp Ala Val Thr Ser Arg
                405                 410                 415

Gln Asp Pro Thr Ser Gln Lys Val Gly Glu Lys Val Phe Pro Ile Trp
                420                 425                 430

Arg
```

```
<210> SEQ ID NO 9
<211> LENGTH: 512
<212> TYPE: PRT
<213> ORGANISM: Artificial Sequence
<220> FEATURE:
<223> OTHER INFORMATION: Human PRMT3

<400> SEQUENCE: 9
```

```
Asp Glu Pro Glu Leu Ser Asp Ser Gly Asp Glu Ala Ala Trp Glu Asp
1               5                   10                  15

Glu Asp Asp Ala Asp Leu Pro His Gly Lys Gln Gln Thr Pro Cys Leu
                20                  25                  30

Phe Cys Asn Arg Leu Phe Thr Ser Ala Glu Glu Thr Phe Ser His Cys
            35                  40                  45

Lys Ser Glu His Gln Phe Asn Ile Asp Ser Met Val His Lys His Gly
        50                  55                  60

Leu Glu Phe Tyr Gly Tyr Ile Lys Leu Ile Asn Phe Ile Arg Leu Lys
65                  70                  75                  80

Asn Pro Thr Val Glu Tyr Met Asn Ser Ile Tyr Asn Pro Val Pro Trp
                85                  90                  95

Glu Lys Glu Glu Tyr Leu Lys Pro Val Leu Glu Asp Leu Leu Leu
                100                 105                 110

Gln Phe Asp Val Glu Asp Leu Tyr Glu Pro Val Ser Val Pro Phe Ser
            115                 120                 125

Tyr Pro Asn Gly Leu Ser Glu Asn Thr Ser Val Val Glu Lys Leu Lys
        130                 135                 140
```

His Met Glu Ala Arg Ala Leu Ser Ala Glu Ala Leu Ala Arg Ala
145                 150                 155                 160

Arg Glu Asp Leu Gln Lys Met Lys Gln Phe Ala Gln Asp Phe Val Met
                165                 170                 175

His Thr Asp Val Arg Thr Cys Ser Ser Thr Ser Val Ile Ala Asp
            180                 185                 190

Leu Gln Glu Asp Glu Asp Gly Val Tyr Phe Ser Tyr Gly His Tyr
        195                 200                 205

Gly Ile His Glu Glu Met Leu Lys Asp Lys Ile Arg Thr Glu Ser Tyr
210                 215                 220

Arg Asp Phe Ile Tyr Gln Asn Pro His Ile Phe Lys Asp Lys Val Val
225                 230                 235                 240

Leu Asp Val Gly Cys Gly Thr Gly Ile Leu Ser Met Phe Ala Ala Lys
                245                 250                 255

Ala Gly Ala Lys Lys Val Leu Gly Val Asp Gln Ser Glu Ile Leu Tyr
            260                 265                 270

Gln Ala Met Asp Ile Ile Arg Leu Asn Lys Leu Glu Asp Thr Ile Thr
        275                 280                 285

Leu Ile Lys Gly Lys Ile Glu Glu Val His Leu Pro Val Glu Lys Val
    290                 295                 300

Asp Val Ile Ile Ser Glu Trp Met Gly Tyr Phe Leu Leu Phe Glu Ser
305                 310                 315                 320

Met Leu Asp Ser Val Leu Tyr Ala Lys Asn Lys Tyr Leu Ala Lys Gly
                325                 330                 335

Gly Ser Val Tyr Pro Asp Ile Cys Thr Ile Ser Leu Val Ala Val Ser
            340                 345                 350

Asp Val Asn Lys His Ala Asp Arg Ile Ala Phe Trp Asp Asp Val Tyr
        355                 360                 365

Gly Phe Lys Met Ser Cys Met Lys Lys Ala Val Ile Pro Glu Ala Val
    370                 375                 380

Val Glu Val Leu Asp Pro Lys Thr Leu Ile Ser Glu Pro Cys Gly Ile
385                 390                 395                 400

Lys His Ile Asp Cys His Thr Thr Ser Ile Ser Asp Leu Glu Phe Ser
                405                 410                 415

Ser Asp Phe Thr Leu Lys Ile Thr Arg Thr Ser Met Cys Thr Ala Ile
            420                 425                 430

Ala Gly Tyr Phe Asp Ile Tyr Phe Glu Lys Asn Cys His Asn Arg Val
        435                 440                 445

Val Phe Ser Thr Gly Pro Gln Ser Thr Lys Thr His Trp Lys Gln Thr
    450                 455                 460

Val Phe Leu Leu Glu Lys Pro Phe Ser Val Lys Ala Gly Glu Ala Leu
465                 470                 475                 480

Lys Gly Lys Val Thr Val His Lys Asn Lys Lys Asp Pro Arg Ser Leu
                485                 490                 495

Thr Val Thr Leu Thr Leu Asn Asn Ser Thr Gln Thr Tyr Gly Leu Gln
            500                 505                 510

<210> SEQ ID NO 10
<211> LENGTH: 348
<212> TYPE: PRT
<213> ORGANISM: Artificial Sequence
<220> FEATURE:
<223> OTHER INFORMATION: Yeast ODP1 Protein Arginine Methyltransferase

<400> SEQUENCE: 10

-continued

```
Met Ser Lys Thr Ala Val Lys Asp Ser Ala Thr Glu Lys Thr Lys Leu
 1               5                  10                  15

Ser Glu Ser Glu Gln His Tyr Phe Asn Ser Tyr Asp His Tyr Gly Ile
            20                  25                  30

His Glu Met Leu Gln Asp Thr Val Arg Thr Leu Ser Tyr Arg Asn
        35                  40                  45

Ala Ile Ile Gln Asn Lys Asp Leu Phe Lys Asp Lys Ile Val Leu Asp
 50                  55                  60

Val Gly Cys Gly Thr Gly Ile Leu Ser Met Phe Ala Ala Lys His Gly
 65                  70                  75                  80

Ala Lys His Val Ile Gly Val Asp Met Ser Ser Ile Ile Glu Met Ala
                85                  90                  95

Lys Glu Leu Val Glu Leu Asn Gly Phe Ser Asp Lys Ile Thr Leu Leu
            100                 105                 110

Arg Gly Lys Leu Glu Asp Val His Leu Pro Phe Pro Lys Val Asp Ile
            115                 120                 125

Ile Ile Ser Glu Trp Met Gly Tyr Phe Leu Leu Tyr Glu Ser Met Met
    130                 135                 140

Asp Thr Val Leu Tyr Ala Arg Asp His Tyr Leu Val Glu Gly Gly Leu
145                 150                 155                 160

Ile Phe Pro Asp Lys Cys Ser Ile His Leu Ala Gly Leu Glu Asp Ser
            165                 170                 175

Gln Tyr Lys Asp Glu Lys Leu Asn Tyr Trp Gln Asp Val Tyr Gly Phe
            180                 185                 190

Asp Tyr Ser Pro Phe Val Pro Leu Val Leu His Glu Pro Ile Val Asp
            195                 200                 205

Thr Val Glu Arg Asn Asn Val Asn Thr Thr Ser Asp Lys Leu Ile Glu
            210                 215                 220

Phe Asp Leu Asn Thr Val Lys Ile Ser Asp Leu Ala Phe Lys Ser Asn
225                 230                 235                 240

Phe Lys Leu Thr Ala Lys Arg Gln Asp Met Ile Asn Gly Ile Val Thr
            245                 250                 255

Trp Phe Asp Ile Val Phe Pro Ala Pro Lys Gly Lys Arg Pro Val Glu
            260                 265                 270

Phe Ser Thr Gly Pro His Ala Pro Tyr Thr His Trp Lys Gln Thr Ile
            275                 280                 285

Phe Tyr Phe Pro Asp Asp Leu Asp Ala Glu Thr Gly Asp Thr Ile Glu
            290                 295                 300

Gly Glu Leu Val Cys Ser Pro Asn Glu Lys Asn Asn Arg Asp Leu Asn
305                 310                 315                 320

Ile Lys Ile Ser Tyr Lys Phe Glu Ser Asn Gly Ile Asp Gly Asn Ser
            325                 330                 335

Arg Ser Arg Lys Asn Glu Gly Ser Tyr Leu Met His
            340                 345
```